United States Patent [19]

Xue et al.

[11] Patent Number: 5,703,092
[45] Date of Patent: Dec. 30, 1997

[54] HYDROXAMIC ACID COMPOUNDS AS METALLOPROTEASE AND TNF INHIBITORS

[75] Inventors: Chu-Biao Xue, Hockessin, Del.; William F. DeGrado, Philadelphia, Pa.; Carl Peter DeCicco, Newark, Del.; Irina Cipora Jacobson, Boothwyn, Pa.

[73] Assignee: The DuPont Merck Pharmaceutical Company, Wilmington, Del.

[21] Appl. No.: 632,863

[22] Filed: Apr. 16, 1996

Related U.S. Application Data

[63] Continuation-in-part of Ser. No. 423,197, Apr. 18, 1995, abandoned.

[51] Int. Cl.$^6$ ............... A61K 31/435; A61K 31/415; C07D 471/04; C07D 235/16
[52] U.S. Cl. ............... 514/303; 514/394; 514/399; 546/334; 546/118; 548/309.7; 548/180; 548/204; 548/217; 548/235; 548/247; 548/253; 548/338.1; 548/375.1; 562/623
[58] Field of Search ............... 546/118, 334; 548/180, 204, 217, 235, 247, 253, 309.7, 333.1, 375.1; 514/303, 394, 399

[56] References Cited

U.S. PATENT DOCUMENTS 5,304,604  4/1994  Davidson et al. ............... 514/238.2

FOREIGN PATENT DOCUMENTS

| 0574758 | 5/1993 | European Pat. Off. . |
| 0575844 | 6/1993 | European Pat. Off. . |
| WO9410990 | 11/1993 | WIPO . |
| 9523790 | 9/1995 | WIPO . |

OTHER PUBLICATIONS

Mankin, Henry J. et al., Biochemical and Metabolic Abnormalities in Articular Cartilage from Osteo–Arthritic Human Hips, Apr. 1970, pp. 424–434.

Ehrlich, Michael G. et al., Correlation Between Articular Cartilage Collagenase Activity and Osteoarthritis, Sep./Oct. 1978, p. 761.

Pelletier, Jean–Pierre et al., Collagenase and Collagenolytic Activity in Human Osteoarthritic Carilage, Jan. 1983, p. 63.

Martel–Pelletier, Johanne et al, Neutral Protease Capable of Proteoglycan Digesting Activity in Osteoarthritic and Noraml Human Articular Cartilage, Mar. 1984, p. 305.

Okada, Yasunori, Localization of Matrix Metalloproteinase 3 (Stromelysin) in Osteoarthritic Cartilage and Synovium, 1992, p. 680.

Wahl, Robert C. & Richard P. Dunlap Biochemistry and Inhibition of Collagenase and Stromelysin, 1990, p. 177.

Ogita, Takeshi et al., Matlystatins, New Inhibiotrs of Typeiv Collagenases from Actinomadura Atramentaria, Nov. 1992, p. 1723.

Stetler–Stevenson, William G., Type IV Collagenases in Tumor Invasion and Metastasis, 1990, p. 289.

J. Med. Chem., "Matrix Metalloproteinase Inhibitors Containing a (Carboxyalkyl)amino Zinc Ligand: Modification of the P1 and P2' Residues", vol. 37, 1994, pp. 674–688.

Primary Examiner—Bernard Dentz
Attorney, Agent, or Firm—Karen H. Kondrad

[57] ABSTRACT

The present invention provides novel hydroxamic acids and carbocyclic acids and derivatives thereof and to pharmaceutical compositions and methods of use of these novel compounds for the inhibition of matrixmetalloproteinases, such as stromelysin and other matrix metalloproteinases, and also inhibit the production of tumor necrosis factor (TNF), and are therefore useful for the treatment of arthritis and other related inflammatory diseases. These novel compounds are represented by Formula I below:

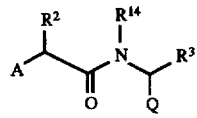

Formula I

11 Claims, No Drawings

HYDROXAMIC ACID COMPOUNDS AS METALLOPROTEASE AND TNF INHIBITORS

CROSS-REFERENCE TO EARLIER FILED APPLICATION

This application is a continuation-in-part of U.S. patent application Ser. No. 08/423,197 filed Apr. 18, 1995 now abandoned. The disclosure of this earlier filed application is hereby incorporated by reference.

FIELD OF THE INVENTION

The present invention relates to small molecules which inhibit matrix metalloproteinases, and the production of tumor necrosis factor (TNF), pharmaceutical preparations containing them and to their use as pharmaceutical agents.

BACKGROUND OF THE INVENTION

There is now a body of evidence that stromelysin (MMP-3) and other metalloproteinases (MMP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of matrix metalloproteinase), which form inactive complexes with the MMP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartillage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, immunohistochemical studies (Okada et al. Ann. Rheum. 48, 1989, 645) have demonstrated that stromelysin is synthesized and secreted by synovial lining cells in RA. Also, higher than normal levels of stromelysin in chondrocytes was detected in 90% of OA cartilage where stromelysin staining correlated with histological scores of pathology and with proteoglycan depletion (Okada et al. Lab Invest. 66, 1992, 680).

Therefore stromelysin, and other matrix metalloproteinase (MMP-3), have been implicated as key enzymes in the destruction of mammalian cartilage and bone. It can be expected that the pathogenesis of such diseases can be modified in a beneficial manner by the administration of MMP inhibitors, and many compounds have been suggested for this purpose (see Wahl et al. Ann. Rep. Med. Chem. 25, 175–184, AP, San Diego, 1990).

Compounds which have the property of inhibiting the action of metalloproteinases involved in connective tissue breakdown such as stromelysin, collagenase, and gelatinase are potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and rumour metastasis, invasion and growth.

Tumour necrosis factor (TNF or TNF-a) is a cytokine which is produced initially as a cell-associated 28 kD precusor. It is released as an active, 17 kD form, which can mediate a large number of deleterious effects in vivo. When administered to animals or humans it causes inflammation, fever, cardiovascular effects, hemorrhage, coagulation, similar to those seen during acute infections and shock states.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore potentially useful for the treatment or prophylaxis of many inflammatory, infectious, immunological or malignant diseases. These include, but are not restricted to septic shock, haemodynamic shock and sepsis syndrome, post ischaemic reperfusion injury, malaria, crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, and hyperoxic alveolar injury.

Since excessive TNF production has been noted in several diseases or conditions also characterized by MMP-mediated tissue degradation, compounds which inhibit both MMPs and TNF production may have particular advantages in the treatment or prophylaxis of diseases or conditions in which both mechanisms are involved.

PCT international Publication No. WO 95/23790 describes imidazoles substituted hydroxamic acid derivatives of the general formula:

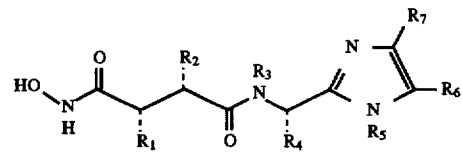

PCT International Publication No. WO 92/213260 describes N-carboxyalkylpeptidyl compounds of general formula:

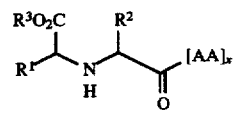

wherein AA is an amino acid, as inhibitors of matrix metallproteinase mediated diseases.

PCT International Publication No. WO 90/05716 discloses hydroxamic acid based collagenase inhibitors having the general formula:

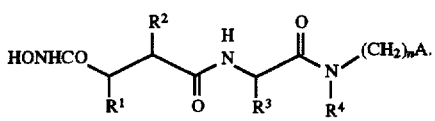

PCT International Publication No. WO 92/13831 describes related hydroxamic acids having collagenase inhibiting activity with the general formula:

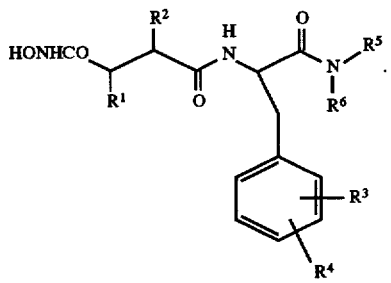

PCT International Publication No. WO 94/02446 discloses metalloproteinase inhibitors which are natural amino acid derivatives of general formula:

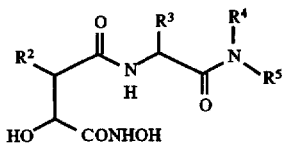

PCT International Publication No. WO 93/09097 discloses piperazinic acid derivatives of general formula:

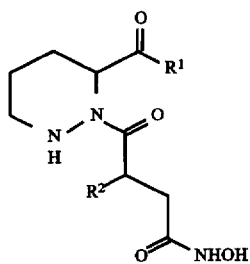

having inhibiting activity against type IV collagenase useful as a cancer metastasis suppressants.

Ogita et al. (J. Anti. 1992, 45, 1723–1732) report the isolation of a structurally related class of microbial metabolites, the matlystatins, which were identified through screening for inhibitors of Type IV collagenases and share the general formula shown below.

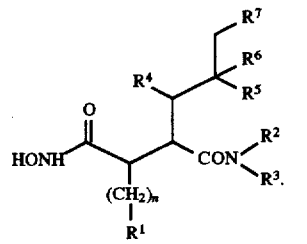

European Patent Application Publication No. 574,758, discloses hydroxamic acid derivatives as collagenase inhibitors having the general formula:

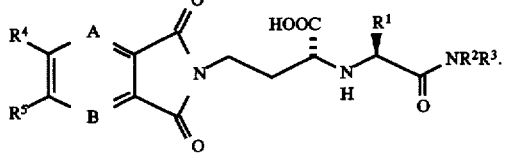

PCT International Publication No. WO 94/00119 discloses aminobutanoic acid compounds having metalloprotease inhibiting properties as shown below:

The compounds of the current invention act as inhibitors of stromelysin and other matrix metalloproteinases, thereby preventing cartilage loss and destruction. In addition, the compounds of the current invention inhibit the production of TNF, a cytokine implicated in inflammatory diseases. The hydroxamic and carboxylic acids and derivatives thereof of the present invention have been further found to be orally bioavailable. A number of the compounds reported to be inhibitors of metalloproteinases, such as collagenase, have suffered from lack of adequate bioavailability and are thus not useful as therapeutic agents, particularly if oral administration is desired. Poor oral activity has been ascribed to relatively high molecular weight, to inadequate solubility properties, and to the presence of peptide bonds, which are vulnerable to cleavage by mammalian proteases in vivo and which generally cause the molecules to be extensively bound in human serum. The hydroxamic and carboxylic acids and derivatives described herein have a distinct advantage in this regard, in that they do not contain readily clearable peptide bonds, are of low molecular weight, and can be hydrophilic yet still inhibit matrix metalloproteinases.

SUMMARY OF THE INVENTION

The present invention provides novel hydroxamic acids and carbocyclic acids and derivatives thereof and to pharmaceutical compositions and methods of use of these novel compounds for the inhibition of matrixmetalloproteinases, such as stromelysin and other matrix metalloproteinases, and also inhibit the production of tumor necrosis factor (TNF), and are therefore useful for the treatment of arthritis and other related inflammatory diseases. These novel compounds are represented by Formula I below:

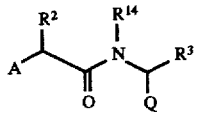

Formula I or pharmaceutically acceptable salts or prodrug forms thereof, wherein:

A is selected from $-N(R^8)C(R^9)(R^{9a})CO_2H$, $-CH(R^{11})C(R^9)(R^{9a})CO_2H$, or $-C(R^1)(R^{1a})CONHOH$;

Q is selected from:
phenyl substituted with 0–3 $R^5$, $R^6$, and/or $R^7$,
pyridyl substituted with 0–3 $R^5$, $R^6$, and/or $R^7$,
triazole substituted with 0–3 $R^5$, $R^6$, and/or $R^7$,
thiazole substituted with 0–3 $R^5$, $R^6$, and/or $R^7$,
oxazole substituted with 0–3 $R^5$, $R^6$, and/or $R^7$,
tetrazole substituted with 0–3 $R^5$, $R^6$, and/or $R^7$,
isoxazole substituted with 0–3 $R^5$, $R^6$, and/or $R^7$,
pyrazole substituted with 0–3 $R^5$, $R^6$, and/or $R^7$,
thiopyrazole substituted with 0–3 $R^5$, $R^6$, and/or $R^7$,
isoxazoline substituted with 0–3 $R^5$, $R^6$, and/or $R^7$,
benzimidazole substituted with 1–3 $R^5$, $R^6$, and/or $R^7$,
benzoxazole substituted with 0–3 $R^5$, $R^6$, and/or $R^7$,
benzothiazole substituted with 0–3 $R^5$, $R^6$, and/or $R^7$.

When A is $-C(R^1)(R^{1a})CONHOH$ and $R^3$ is a cyclohexyl, cyclohexylmethyl, naphthyl, Q can also be a benzimidazole substituted with 0–3 $R^5$, $R^6$, and/or $R^7$, or an imidazole substituted with 0–3 $R^5$, $R^6$, and/or $R^7$.

When A is $-N(R^8)C(R^9)(R^{9a})CO_2H$ or $-CH(R^{11})C(R^9)(R^{9a})CO_2H$, Q can also be a benzimidazole substituted with 0–3 $R^5$, $R^6$, and/or $R^7$ or an imidazole substituted with 0–3 $R^5$, $R^6$, and/or $R^7$.

The phenyl ring of the benzimidazole, benzoxazole and benzothiazole can be optionally interrupted with 1–2 nitrogens.

$R^1$ and $R^{1a}$ are independently selected from:
H, halogen, $OR^{17}$, $NR^{10}R^{10a}$, $NR^8R^{10a}$, $S(O)_mR^{17a}$,
$C_1$–$C_4$ alkyl substituted with 0–3 $R^4$,
$C_2$–$C_4$ alkenyl substituted with 0–3 $R^4$,
$C_2$–$C_4$ alkynyl substituted with 0–3 $R^4$,
$C_6$–$C_{10}$ aryl substituted with 0–3 $R^{18}$,
a $C_5$–$C_{11}$ heterocycle containing from 1–4 heteroatoms selected from N, O or S, said heterocycle optionally substituted with 0–3 $R^{18}$, or
$C_3$–$C_8$ cycloalkyl, Alternately, $R^1$ and $R^{1a}$ can be taken together to form a 3–7 membered carbocyclic or heterocyclic, said heterocyclic ring containing from 1–2 heteroatoms selected from N, O or S;

$R^2$ is selected from:
H
$C_1$–$C_6$ alkyl substituted with 0–3 $R^{17b}$,
$-O-(C_1-C_8 \text{ alkyl})-R^{20}$,
$-S-(C_1-C_8 \text{ alkyl})-R^{20}$,
$-CH_2O-(C_1-C_8 \text{ alkyl})-R^{20}$, or
$-CH_2S-(C_1-C_8 \text{ alkyl})-R^{20}$;

$R^3$ is selected from:
H,
$C_1$–$C_6$ alkyl substituted with 0–3 $R^{17b}$,
$-(C_1-C_6 \text{ alkylene})-OR^{12}$,
$-(C_1-C_6 \text{ alkylene})-SR^{12}$, $C_6$–$C_{10}$ aryl substituted with 0–3 $R^{18}$, or
$C_3$–$C_7$ cycloalkyl;

$R^4$ is selected from:
$-OR^{17}$, $-SO_mR^{17}$, $-NR^8R^{10}$, $-NHC(=NR^8)N(R^8)R^{10}$,
$C_1$–$C_4$ alkyl,
aryl substituted with 0–5 $R^{18}$,
$C_3$–$C_8$ cycloalkyl, or
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

$R^5$ is selected from:
hydrogen, halogen, $C_1$–$C_4$ haloalkyl, hydroxy, $C_1$–$C_4$ alkoxy, $-NR^{14}R^{15}$, or $C_1$–$C_6$ alkyl substituted with 0–3 $R^{20}$;

$R^6$ and $R^7$ are indendently selected from:
H, $C_1$–$C_4$ alkyl, or $C_6$–$C_{10}$ aryl;
Alternately, $R^6$ and $R^7$ may be taken together to be
1,2-phenylene substituted with 0–2 $R^5$,
2,3-pyridinylene substituted with 0–2 $R^5$,
3,4-pyridinylene substituted with 0–2 $R^5$, or
5,6-pyrimidinylene substituted with 0–2 $R^5$;

$R^8$ is a substituent on nitrogen and is selected from hydrogen,
$C_1$–$C_6$ alkyl substituted with 0–3 $R^{20}$,
$C_1$–$C_6$-alkylcarbonyl,
alkoxycarbonyl,
arylalkoxycarbonyl,
alkylaminocarbonyl,
arylsulfonyl,
heteroarylalkoxycarbonyl,
cycloalkoxycarbonyl,
heteroarylsulfonyl,
alkylsulfonyl, or
cycloalkylsulfonyl;

$R^9$ and $R^{9a}$ are independently selected from:
H, halogen, $OR^{17}$, $NR^{10}R^{10a}$, $NR^8R^{10a}$, $S(O)_mR^{17a}$,
$C_1$–$C_4$ alkyl substituted with 0–3 $R^4$,
$C_2$–$C_4$ alkenyl substituted with 0–3 $R^4$,
$C_2$–$C_4$ alkynyl substituted with 0–3 $R^4$,
$C_6$–$C_{10}$ aryl substituted with 0–3 $R^{18}$,
a $C_5$–$C_{11}$ heterocycle containing from 1–4 heteroatoms selected from N, O or S, said heterocycle optionally substituted with 0–3 $R^{18}$, or
$C_3$–$C_8$ cycloalkyl, Alternately, $R^9$ and $R^{9a}$ can be taken together to form a 3–7 membered carbocyclic or heterocyclic, said heterocyclic ring containing from 1–2 heteroatoms selected from N, O or S;

$R^{10}$ is selected from:
hydrogen,
$C_1$–$C_4$ alkoxy,
$C_1$–$C_6$ alkyl substituted with 0–4 $R^4$;
$R^{10a}$ is selected from hydrogen or $C_1$–$C_4$ alkyl;
$R^{10}$ and $R^{10a}$ can alternatively join to form $-(CH_2)_4-$, $-(CH_2)_5-$, $-CH_2CH_2N(R^{18})CH_2CH_2-$, or $-CH_2CH_2OCH_2CH_2-$;

$R^{11}$ is H, or $C_1$–$C_4$ alkyl;
$R^{12}$ is $C_1$–$C_4$ alkyl or $C_6$–$C_{10}$ aryl;
$R^{14}$ and $R^{15}$ are independently selected from H or $C_1$–$C_4$ alkyl;
$R^{17}$ is selected from:

hydrogen,
$C_1$–$C_6$ alkyl substituted with 0–3 $R^{17a}$
$C_1$–$C_6$ alkylcarbonyl substituted with 0–3 $R^{17a}$,
$C_1$–$C_6$ alkoxycarbonyl substituted with 0–3 $R^{17a}$,
phenoxycarbonyl substituted with 0–3 $R^{18}$;
$R^{17a}$ is selected from:
H,
$C_1$–$C_4$ alkyl,
aryl substituted with 0–5 $R^{18}$,
$C_3$–$C_8$ cycloalkyl
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

$R^{17b}$ is selected from:
aryl substituted with 0–5 $R^{18}$,
$C_3$–$C_8$ cycloalkyl
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

$R^{18}$, when a substituent on carbon, is selected from one or more of the following:
phenoxy, benzyloxy, halogen, hydroxy, nitro, cyano, $C_1$–$C_4$ alkyl, $C_1$–$C_4$ alkoxy, —$CO_2H$, sulfonamide, $C_1$–$C_4$ alkyl substituted with —$NR^{10}R^{10a}$, —$NR^{10}R^{10a}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{11}$, —$NHSO_2R^{11}$,
phenyl, optionally substituted with halogen, $C_1$–$C_4$ alkyl, $C_1$–$C_4$ alkoxy, hydroxy or $NR^{10}R^{10a}$,
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;
or $R^{18}$ may be a 3- or 4- carbon chain attached to adjacent carbons on the ring to form a fused 5- or 6-membered ring, said 5- or 6- membered ring being optionally substituted with halogen, $C_1$–$C_4$ alkyl, $C_1$–$C_4$ alkoxy, hydroxy, —$NR^{10}R^{10a}$, =O or =S when attached to a saturated carbon atom, or =O when attached to sulfur;

$R^{18}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{10}R^{10a}$, —$NR^{10}R^{10a}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl;

$R^{20}$ is selected from:
aryl substituted with 0–5 $R^{18}$,
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

Presently more preferred compounds of this invention are compounds of formula I wherein:
$R^1$ is selected from:
H
$C_1$–$C_4$ alkyl substituted with 0–3 $R^4$;
$R^2$ is selected from:
$C_2$–$C_4$ alkyl substituted with 0–3 $R^{17b}$,
—O—($C_1$–$C_6$ alkyl)—$R^{20}$,
—S—($C_1$–$C_6$ alkyl)—$R^{20}$,
—$CH_2O$—($C_1$–$C_5$ alkyl)—$R^{20}$, or
—$CH_2S$—($C_1$–$C_5$ alkyl)—$R^{20}$;
$R^3$ is selected from:
H, or
$C_1$–$C_6$ alkyl substituted with 0–3 $R^4$,
and all other variables are as defined above.

Specifically preferred compounds of this embodiment are selected from the group consisting of:
N-[1(S)-(5-azabenzimidazol-2-yl)-2-(2-naphthyl)ethyl]-[3-hydroxyaminocarbonyl)-2(R)-isobutyl-3(S)-methyl]propanamide
N-[1(S)-(2-imidazolyl)-2-(2-naphthyl)ethyl]-[3-hydroxyaminocarbonyl)-2(R)-isobutyl-3(S)-methyl]propanamide
N-[1(S)-(5-methoxy-2-Benzimidazolyl)-3-methylbutyl]-[3-(N-hydroxyaminocarbonyl)-2(R)-isobutyl-(3S)-methyl]propanamide,
N-[1(S)-(5-methoxy-2-benzimidazolyl)-2-phenylethyl]-[3-(N-hydroxyaminocarbonyl)-3(S)-hydroxy-2(R)-isobutyl]propanamide,
N-[1(S)-(5-methoxy-2-benzimidazolyl)-2,2,2-trimethylethyl]-[3-(N-hydroxyaminocarbonyl)-3(S)-hydroxy-2(R)-isobutyl]propanamide,
N-[1(S)-(5-chloro-2-benzimidazolyl)-2,2,2-trimethylethyl]-[3-(N-hydroxyaminocarbonyl)-3(S)-hydroxy-2(R)-isobutyl]propanamide,
N-[1(S)-(5-azabenzimidazol-2-yl)-2-(2-naphthyl) ethyl]-[3-(N-hydroxyaminocarbonyl)-3(S)-hydroxy-2(R)-isobutyl]propanamide,
N-[1(S)-(5-azabenzimidazol-2-yl)-2-(2-naphthyl) ethyl]-[3-(N-hydroxyaminocarbonyl)-3(S)-(2-picolyloxy)-2(R)-isobutyl]propanamide,
N-[1(S)-(5-azabenzimidazol-2-yl)-2-(2-naphthyl)ethyl]-[3-(N-hydroxyaminocarbonyl)-3(S)-(3-picolyloxy)-2(R)-isobutyl]propanamide,
N-[1(S)-(5-azabenzimidazol-2-yl)-2-(2-naphthyl)ethyl]-[3-(N-hydroxyaminocarbonyl)-3(S)-(4-picolyloxy)-2(R)-isobutyl]propanamide,
N-[1(S)-(5-azabenzimidazol-2-yl)-2-(2-naphthyl)ethyl]-[3-(N-hydroxyaminocarbonyl)-3(S)-benzyloxy-2(R)-isobutyl]propanamide,
N-[1(S)-(5-azabenzimidazol-2-yl)-2-(2-naphthyl)ethyl]-[3-(N-hydroxyaminocarbonyl)-3(S)-methyl-2(R)-isobutyl]propanamide,
N-[1(S)-(5-azabenzimidazol-2-yl)-2-(2-naphthyl)ethyl]-[3-(N-hydroxyaminocarbonyl)-3(S)-phenpropyl-2(R)-isobutyl]propanamide,
N-[1(S)-(5-azabenzimidazol-2-yl)-2-(2-naphthyl)ethyl]-[3-(N-hydroxyaminocarbonyl)-3(S)-(2-pyridylpropyl)-2(R)-isobutyl]propanamide,
N-[1(S)-(5-azabenzimidazol-2-yl)-2-(2-naphthyl)ethyl]-[3-(N-hydroxyaminocarbonyl)-3(S)-propargyl-2(R)-isobutyl]propanamide, N-[1(S)-(5-azabenzimidazolyl)-2-(2-naphthyl)ethyl]-[3-(N-hydroxyaminocarbonyl)-3(S)-allyl-2(R)-isobutyl]propanamide, N-[1(S)-(5-azabenzimidazolyl)-2-(2-naphthyl)ethyl]-[3-(N-hydroxyaminocarbonyl)-3(S)-(1-pyrazolylpropyl)-2(R)-isobutyl]propanamide, N-[1(S)-(5-azabenzimidazolyl)-2-(2-naphthyl)ethyl]-[3-(N-hydroxyaminocarbonyl)-3(S)-(1-imidazolylpropyl)-2(R)-isobutyl]propanamide, 1(R)-{1(S)-[1(S)-(2-benzimidazolyl)-2-methylpropylaminocarbonyl]-3-phenylpropylamino}-3-(p-toluenesulfonylamino)butyric acid, 1(R)-{1(S)-[1(S)-(2-benzimidazolyl)-2-phenylethylaminocarbonyl]-3-phenylpropylamino}-3-(p-toluenesulfonylamino)butyric acid, 1(R)-{1(S)-[1(S)-(2-benzimidazolyl)ethylaminocarbonyl]-3-phenylpropylamino}-3-(p-toluenesulfonylamino)butyric acid, 1(R)-{1(S)-[1(S)-(2-benzimidazolyl)-3-methylbutylaminocarbonyl]-3-phenylpropylamino}-3-(p-toluenesulfonylamino)butyric acid, 1(R)-{1(S)-[1(S)-(2-benzimidazolyl)-2-methylbutylaminocarbonyl]-3-phenylpropylamino}-3-(p-toluenesulfonylamino)butyric acid, N-[[1-(2-benzimidazolyl)-2-phenyl]ethyl]-2-[[2-(1,1'-biphenyl)yl]ethyl]-4-carboxyoctanamide, N-[[1-(2-imidazolyl)-2-phenyl]ethyl]-2-[[2-(1,1'-biphenyl)yl]ethyl]-4-carboxyoctanamide and 2(R)-n-butyl-4-(2-(1,1'-biphenylethyl)-4-[1S-(2-imidazole)neopentylaminocarbonyl]butyric acid trifluoroacetate

DETAILED DESCRIPTION OF THE INVENTION

In the present invention it has been discovered that the compounds above are useful as inhibitors of stromelysin and similar matrix metalloproteinases, and for the treatment of rheumatoid arthritis, osteoarthritis and similar pathological conditions.

The present invention also provides methods for the treatment of osteo- and rheumatoid arthritis by administering to a host a pharmaceutically or therapeutically effective or acceptable amount of a compound of formula (I) as described above. By therapeutically effective amount, it is meant an amount of a compound of the present invention effective to inhibit stromelysin or to treat the symptoms of osteo- or rheumatoid arthritis in a host.

The compounds of the present invention can also be administered in combination with one or more additional therapeutic agents. Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

By "therapeutically effective amount" it is meant an amount of a compound of Formula I that when administered alone or in combination with an additional therapeutic agent to a cell or mammal is effective to inhibit stromelysin so as to prevent or ameliorate the inflamatory disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example $R^1$ through $R^{20}$, $R^{10a}$, n, m, Z, X, etc.) occurs more than one time in any constituent or in any formula, its definition on each occurrence is independent of its definition at every other occurrence. Thus, for example, if a group is shown to be substituted with 0–3 $R^{17}$, then said group may optionally be substituted with up to three $R^{17}$ and $R^{17}$ at each occurrence is selected independently from the defined list of possible $R^{17}$.

When a bond to a substituent is shown to cross the bond connecting two atoms in a ring, then such substituent may be bonded to any atom on the ring.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or polycyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0] bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "—(alkyl)—", "—(alkyenyl)—" and "—(phenyl)—", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" or "carbocyclic ring system" is intended to mean any stable 3- to 7-membered monocyclic or bicyclic or 7- to 14-membered bicyclic or tricyclic or up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, hexahydropyridazinyl, indolinyl, isoindolinyl, quinuclidinyl, morpholinyl or oxazolidinyl. Also included are fused ring and spiro compounds containing, for example, the above heterocycles.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, phosphate esters, dimethylglycine esters, aminoalkylbenzyl esters, aminoalkyl esters and carboxyalkyl esters of alcohol and phenol functional groups in the compounds of formula (I); and the like.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoniumhydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the educt molecule must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternate methods must then be used.

Compounds of formula I wherein A is HONHCOCH(R$^1$) are prepared by condensation of acids of formula (II):

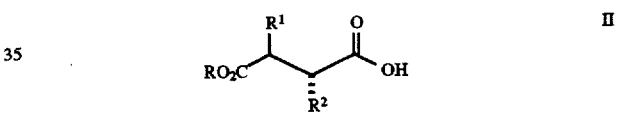

wherein R is an ester protecting group, and R$^1$ and R$^2$ are defined as provided in the preceding Summary of the Invention in connection with formula I, with an appropriately substituted amine to form an amide bond as shown in Scheme 1.

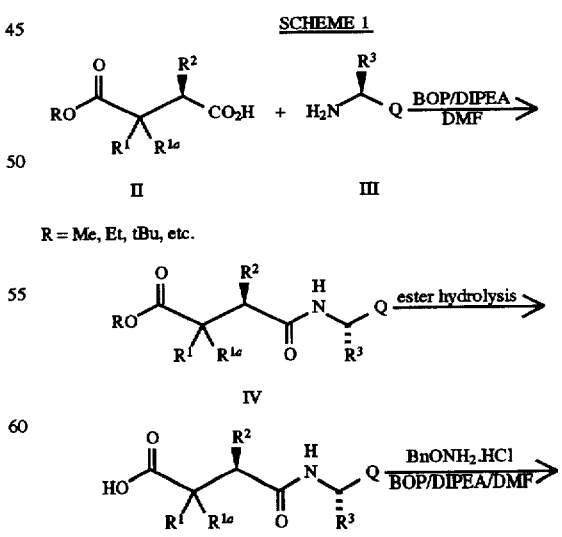

-continued
SCHEME 1

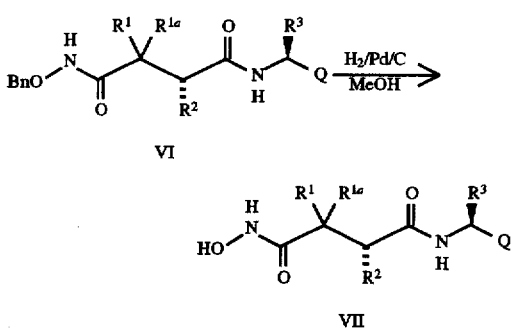

The condensation is carried out using any of the many methods for the formation of amide bonds known to one skilled in the art of organic synthesis. These methods include but are not limited to conversion of acid (II) to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole. Removal of the ester protecting group using methods well known to one skilled in the art of organic synthesis, followed by activation the resulting acid, for example with BOP-Cl, and reaction with O-benzylhydroxylamine gives a benzyl-protected hydroxamic acid. Catalytic hydrogenolysis provides the target hydroxamic acid.

The acids of formula (II) are prepared by methods described in the literature (Crimmin et al Synlett 1993, 137; Tamaki et al Tetrahedron Lett 1993, 34:683) or by the general routes shown in Scheme 2. An appropriately activated (e.g. X=Cl) carboxylic acid derivative (VIII) is converted to the chiral oxazolidinone (IX) by the method of Evans (JACS, 1982, 104, 1737). Deprotonation with a strong base followed by treatment with t-butylbromoacetate, produces intermediate (X). Hydrolysis of the chiral auxilliary can be accomplished with alkaline hydrogen peroxide to give acid (Va) where $R^1$ and $R^{1a}$ are both hydrogen.

SCHEME 2

Method A.

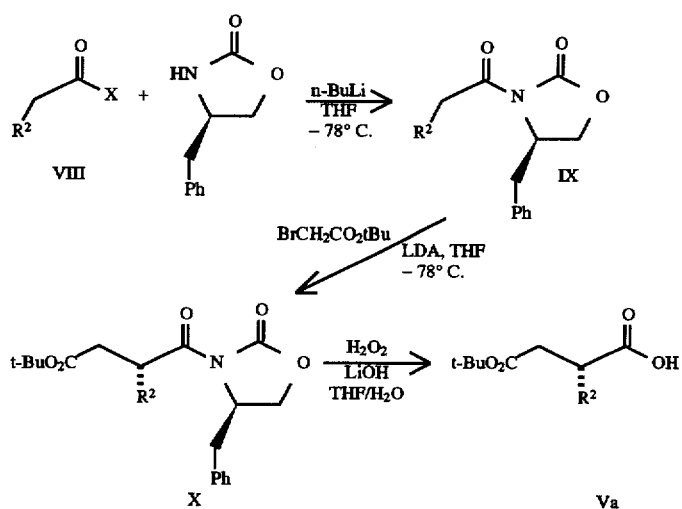

Method B.

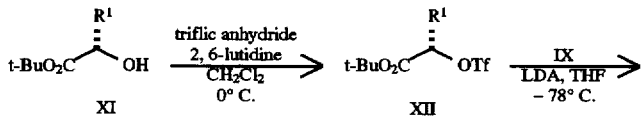

-continued
SCHEME 2

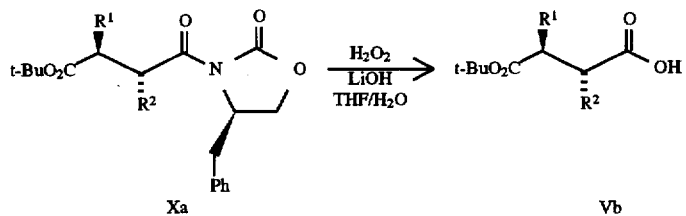

Method C.

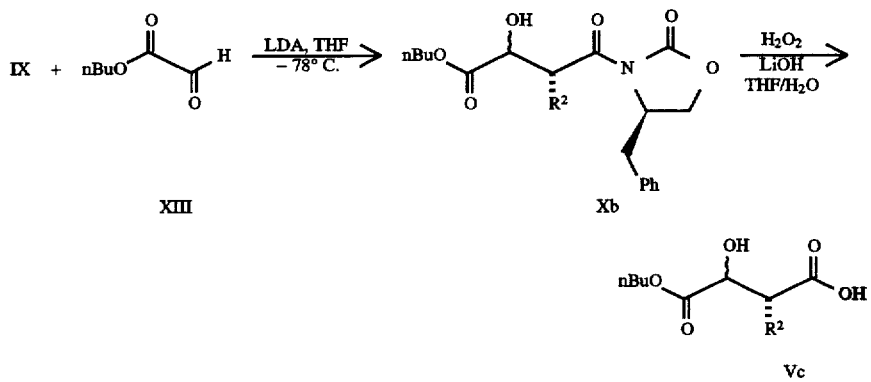

Method D.

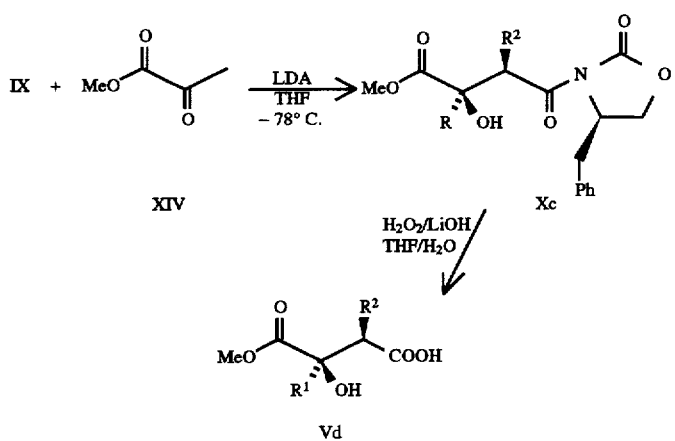

Alternately, in method B, an a-hydroxyacid of formula XI is converted to the corresponding triflate. Alkylation of chiral oxazolidinone IX with XI provides intermediate XIII which after removal of the chiral auxilliary provides acid Vb. Condensation of IX with n-butyl glyoxalate or a-ketoesters gives acids Vc and Vd where $R^1$ is hydroxy and $R^{1a}$ is hydrogen or alkyl respectively.

Amines of formula III wherein Q is a heterocyclic moiety can be prepared from appropriately N-protected amino acids by conversion of the carboxylic acid to the desired heterocycle. Examples of the synthesis of suitable amines are outlined in Schemes 3 and 4.

Treatment of CBz-protected amino acids, XV, with phenylene diamines XVI in the presence of a suitable amide bond forming reagent, such as TBTU, followed by cyclization gives benzimidazole compounds of formula XVII. Temoval of the Cbz protecting groups by standard methods provides amine IIIa wherein Q is a 2-benzimidazolyl group.

Scheme 3

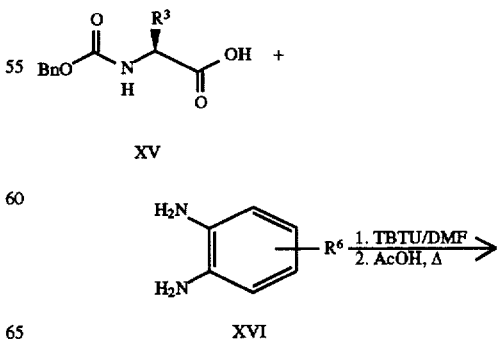

Scheme 3 (continued)

XVII → IIIa (H₂/Pd/C, MeOH)

Alternately, as shown in Scheme 4, Cbz-amino acids, XV can be converted to the corresponding Weinreb amides XVIII by treatment with an activating agent and N,O-dimethylhydroxylamine (reference). Reduction with lithium aluminum hydride provides the aldehyde, XIX, which upon treatment with glyoxal and ammonia yields imidazole XX (reference). Deprotection provides amines, IIIb, wherein Q is 2-imidazolyl. Substituted imidazoles can be obtained by direct chlorination of XX with N-chlorosuccinimide or by direct synthesis from XIX as shown in Scheme 4 Method C.

Scheme 4

Method A.

XV → XVIII (methylchloroformate, CH₃NHOCH₃)
XVIII → XIX (LiAlH₄, THF)
XIX → XX (glyoxal, NH₃, MeOH)
XX → IIIb (H₂ Pd/C, MeOH)

Method B.

XX →(NCS) XXI →(H₂/Pd/C, MeOH)

Scheme 4 (continued)

IIIc

Method C.

XIX + CF₃C(O)CHBr₂ →(NH₄OH, MeOH/H₂O) XXIz →(H₂,Pd/C, MeOH) IIId

Compounds of Formula I wherein A is —NHCH(R⁹)CO₂H are prepared by condensation of acids (XXII) with amines III in the presence of an activating agent such as TBTU, followed by hydrolysis of the ester protecting group as depicted in Scheme 5.

Scheme 5

RO₂C-CH(R⁹)-NH-CH(R²)-CO₂H + H₂N-CH(R³)-Q →(TBTU/DIPEA, DMF) → [amide intermediate] →(ester hydrolysis) → HO₂C-CH(R⁹)-NH-CH(R²)-C(O)-NH-CH(R³)-Q Acids of formula XXII are prepared from protected amino acids as shown in Scheme 6 method A.

Scheme 6

Method A. For R² = —(CH₂)₂NHSO₂R tBuO-C(O)-NH-CH(CONH₂)-CO₂H + Ac₂O →(Pyridine) XXII

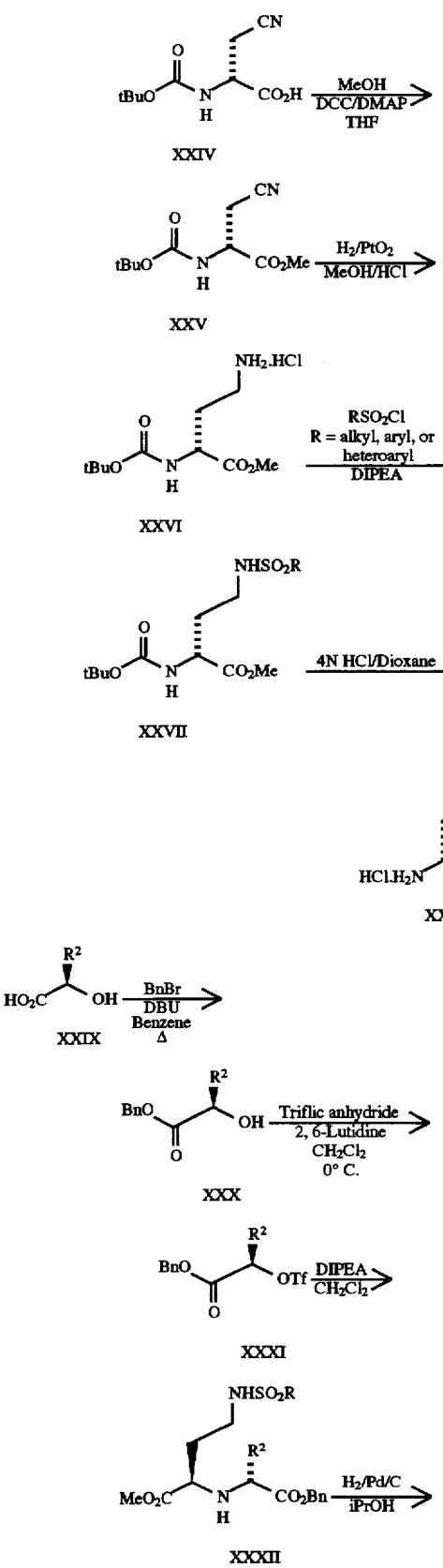
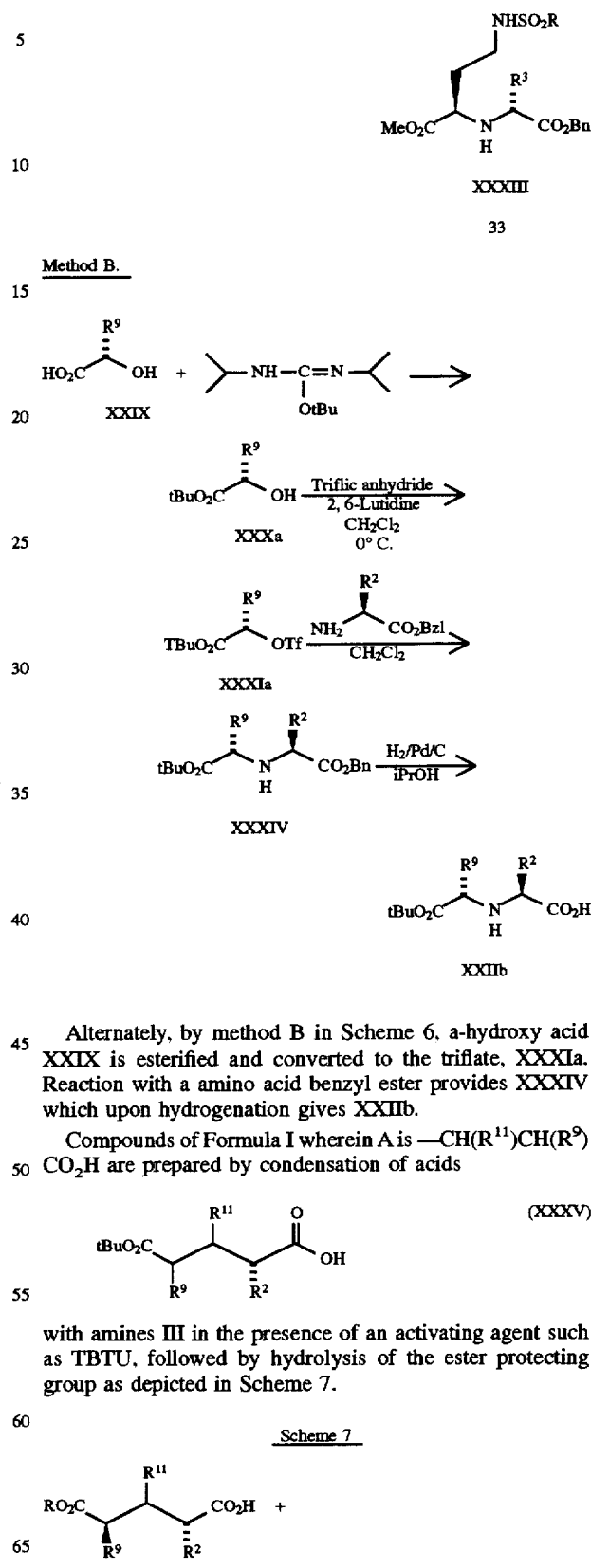

Alternately, by method B in Scheme 6, a-hydroxy acid XXIX is esterified and converted to the triflate, XXXIa. Reaction with a amino acid benzyl ester provides XXXIV which upon hydrogenation gives XXIIb.

Compounds of Formula I wherein A is —CH($R^{11}$)CH($R^9$)$CO_2H$ are prepared by condensation of acids with amines III in the presence of an activating agent such as TBTU, followed by hydrolysis of the ester protecting group as depicted in Scheme 7.

23
-continued
Scheme 7

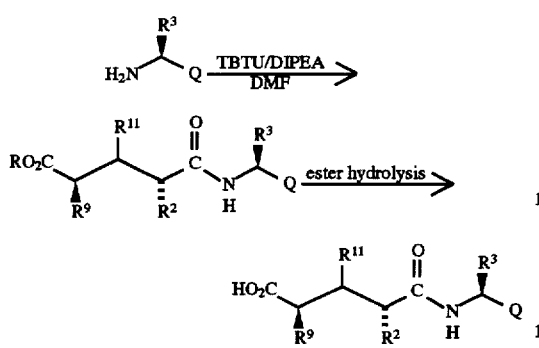

Acids of formula XXXV can be prepared by methods known in the art or for example, as illustrated in Scheme 8 for $R^2$=ArCH$_2$CH$_2$—.

Scheme 9

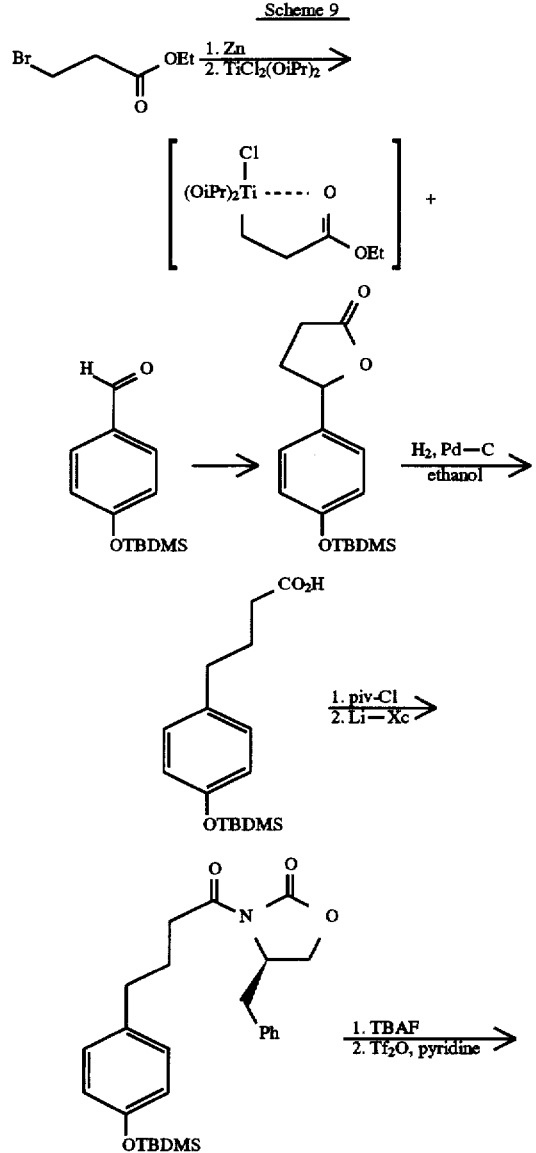

24
-continued
Scheme 9

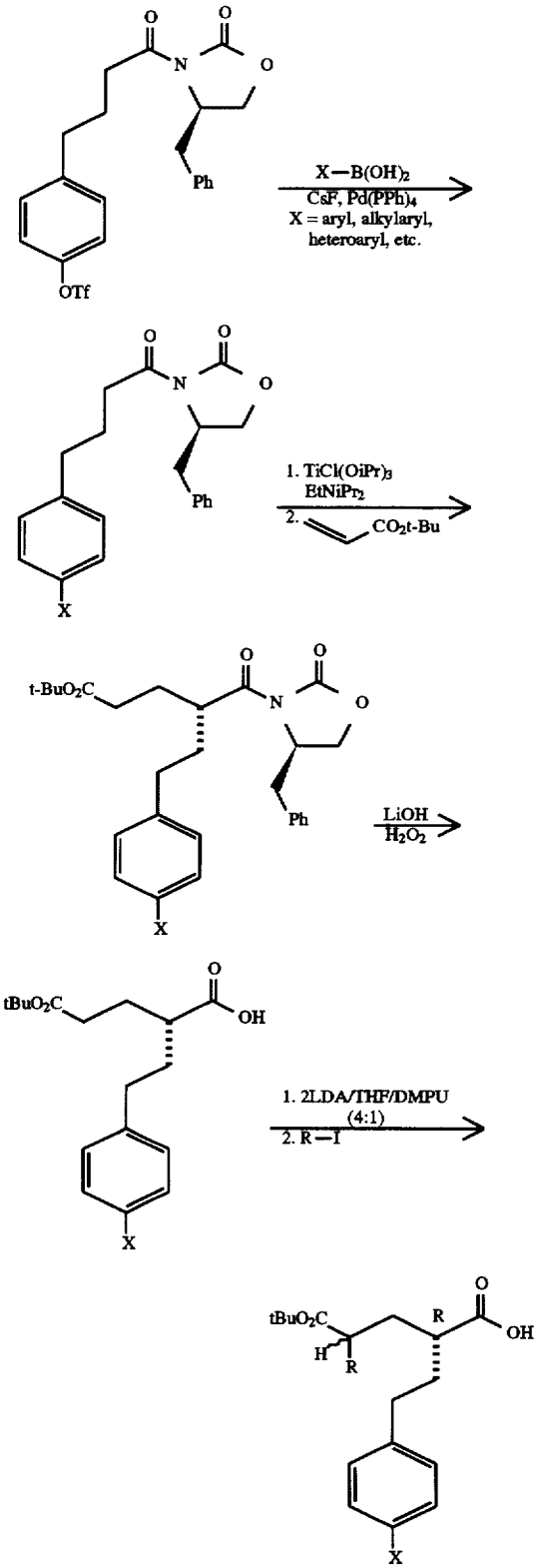

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in Cheung et al. (*Can. J. Chem.* 55, 906 (1977)) and Freidinger et al., (*J. Org. Chem.* 48, 77 (1982)), which are incorporated herein by reference.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference.

In a second aspect of this invention, we claim that pharmaceutical preparations of compounds of formula I (with the indicated provisos) are orally bioavailable drugs useful for the treatment of arthritis by their action as cartilage protectants.

The compounds of this invention and their preparation can be further understood by the following procedures and examples, which exemplify but do not constitute a limit of their invention.

EXAMPLES

Abbreviations used in the Examples are defined as follows: "1×" for once, 2×" for twice, "3×" for thrice, "bs" for broad singlet, "°C" for degrees Celsius, "Cbz" for benzyloxycarbonyl, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "$^1$H" for proton, "hr" for hour or hours, "m" for multiplet, "M" for molar, "min" for minute or minutes, "mp" for melting point range, "MHz" for megahertz, "MS" for mass spectroscopy, "nmr" or "NMR" for nuclear magnetic resonance spectroscopy, "t" for triplet, "tlc" for thin layer chromatography, "v/v" for volume to volume ratio. "a", "b", "R" and "S" are stereochemical designations familiar to those skilled in the art.

Example 33

N-[1(S)-(5-methoxy-2-benzimidazolyl)-3-methylbutyl]-[3-(N-hydroxyaminocarbonyl)-2(R)-isobutyl-(3S)-methyl]propanamide (a). N-benzyloxycarbonyl-1(S)-(5-methoxybenzimidazol-2-yl)-3-methylbutylamine To a mixture of N-benzyloxycarbonyl-L-leucine (20 mmol, 5.3 g), 4-methoxy-1,2-phenylenediamine dihydrochloride (4.22 g, 20 mmol) and O-benzotriazole-N,N,N',N'-tetramethyl-uronium-tetrafluoroborate (TBTU) (6.58 g, 20.50 mmol) in 15 mL DMF cooled in an ice bath was added diisopropylethylamine (14 mL, 80 mmol). After stirring for 2 hours, ethyl acetate was added and the solution was washed with saturated NaHCO$_3$ 3 times and brine 3 times, dried (MgSO$_4$), and concentrated. The crude product was dissolved in 30 mL acetic acid and the solution was heated at 65° C. for 2 hours. Acetic acid was removed by concentration under reduced pressure and the residue was purified on a silica gel column using methanol (3%)-methylene chloride as eluent to give 5.5 g (80%) product. m.p. 73°–77° C. ES-MS: calcd M+1 368.2; found 368.3.

(b) 1(S)-(5-methoxybenzimidazol-2-yl)-3-methylbutylamine hydrochloride.

N-Benzyloxycarbonyl-[1(S)-(5-methoxybenzimidazol-2-yl)-3-methylbutylamine (5.2 g, 14.2 mmol) was hydrogenated at atmospheric pressure in 25 mL methanol containing 1.2 mL concentrated HCl for 1 hour using 10% Pd/C (460 mg) as the catalyst. The catalyst was filtered off and the solution was concentrated. The residue was washed with ether to give 3.8 g (100%) product. m.p. 128°–130° C. ES-MS: calcd M+1 234.2; found 234.4.

(c) N-[1(S)-(5-methoxybenzimidazol-2-yl)-3-methylbutyl]-[3-t-butyloxycarbonyl-2(R)-isobutyl-3(S)-methyl]propanamide.

3-tert-Butoxycarbonyl-2(R)-isobutylpropanoic acid (0.3 g, 1.2 mmol) and 1(S)-(5-methoxybenzimidazol-2-yl)-3-methylbutylamine hydrochloride (0.33 g, 1.23 mmol) were dissolved in 3 mL DMF and the solution was cooled in an ice bath. To it were added TBTU (0.39 g, 1.2 mmol) and diisopropylethylamine (0.64 mL, 3.7 mmol). The mixture was stirred at room temperature for 2 hours and diluted with ethyl acetate. The solution was washed with 5% citric acid, brine, saturated NaHCO$_3$ and brine, dried (MgSO$_4$), and concentrated to give a solid. The solid was purified on a silica gel column to give 0.52 g (92%) product. ES-MS: calcd M+1 460.4; found 460.3.

(d) N-[1(S)-(5-methoxybenzimidazol-2-yl)-3-methylbutyl]-[3-carboxy-2(R)-isobutyl-3(S)-methyl]propanamide.

The compound of Ex. 1, Part c (0.4 g, 0.87 mmol) was dissolved in 10 mL trifluoroacetic acid containing 0.5 mL water and after 1 hours, the solution was concentrated. The residue was taken up in ethyl acetate and the solution was washed with brine 3 times, dried (MgSO$_4$), and concentrated to give a solid. The solid was washed with ether to give 0.35 g (98%) product. ES-MS: calcd M+1 404.5; found 404.3.

(e) N-[1(S)-(5-methoxybenzimidazol-2-yl)-3-methylbutyl]-[3-(N-benzyloxyaminocarbonyl)-2(R)-isobutyl-3(S)-methyl]propanamide.

To a mixture of compound of Ex. 1, Part d (0.32 g, 0.79 mmol), O-benzylhydroxylamine hydrochloride (128 mg, 0.8 mmol) and TBTU (260 mg, 0.8 mmol) in 3 mL DMF cooled in an ice bath was added diisopropylethylamine (0.53 mL, 3.4 mmol) and the mixture was stirred at room temperature for 2 hours. Ethyl acetate was added and the solution was washed with 5% citric acid, brine, NaHCO$_3$ and brine, dried (MgSO$_4$), and concentrated. Purification on a silica gel column gave 180 mg (45%) product. ES-MS: calcd M+1 509.4; found 509.3.

(f) N-[1(S)-(5-methoxybenzimidazol-2-yl)-3-methylbutyl]-[3-(N-hydroxyaminocarbonyl)-2(R)-isobutyl-3(S)-methyl]propanamide.

N-[1(S)-(5-methoxybenzimidazol-2-yl)-3-methylbutyl]-[3-(N-benzyloxyaminocarbonyl)-2(R)-isobutyl-3(S)-methyl]propanamide (140 mg, 0.27 mmol) was hydrogenated at atmospheric pressure in 50 mL methanol for 1.5 hour using 14 mg 10% Pd/C as the catalyst. The catalyst was filtered off and the solution was concentrated to give a solid. The solid was washed with ether to give 102 mg (90%) product. ES-MS: calcd M+1 419.3; found 419.3.

Example 39

N-[1(S)-(5-azabenzimidazol-2-yl)-2-(2-naphthyl)ethyl]-[3-hydroxyaminocarbonyl)-2(R)-isobutyl-3(S)-methyl]propanamide This compound was prepared in a manner analogous to that described in Ex. 33. ES-MS: calcd M+1 474.3; found 474.3.

Example 66

N-[1(S)-(2-immidazolyl)-2-(2-naphthyl)ethyl]-[3-hydroxyaminocarbonyl)-2(R)-isobutyl-3(S)-methyl]propanamide This compound was prepared in a manner analogous to that described in Ex. 33. ES-MS: calcd M+1 423.3; found 423.4.

Example 77

N-[1(S)-(5-methoxybenzimidazol-2-yl)-2-phenylethyl]-[3-(N-hydroxyaminocarbonyl)-3(S)-hydroxy-2(R)-isobutyl]propanamide This compound was prepared in a manner analogous to that described in Example 33. ES-MS: calcd M+1 455.3; found 455.2.

Example 79

N-[1(S)-(5-methoxy-2-benzimidazolyl)-2,2,2-trimethylethyl]-[3-(N-hydroxyaminocarbonyl)-3(S)-hydroxy-2(R)-isobutyl]propanamide This compound was prepared in a manner analogous to that described in Example 33. ES-MS: calcd M+1

Example 86

N-[1(S)-(5-chloro-2-benzimidazolyl)-2,2,2-trimethylethyl]-[3-(N-hydroxyaminocarbonyl)-3(S)-hydroxy-2(R)-isobutyl]propanamide This compound was prepared in a manner analogous to that described in Example 33. ES-MS: calcd M+1

Example 300

1(R)-{1(S)-[1(S)-(2-benzimidazolyl)-2-methylpropylaminocarbonyl]-3-phenylpropylamino}-3-(p-toluenesulfonylamino)butyric acid (a) N-Butyloxycarbonyl-3-cyano-D-alanine N-Butyloxycarbonyl-D-asparagine (25 g, 108 mmol) was dissolved in 200 mL pyridine and 14 mL acetic anhydride and the solution was allowed to stir overnight at room temperature. After most of the pyridine was removed under reduced pressure, ethyl acetate was added and the solution was washed with citric acid and brine, dried (MgSO$_4$), and concentrated to give 21 g (91%) oily product. ES-MS: calcd M+1 215.0; found 215.0.

(b) N-Butyloxycarbonyl-3-cyano-D-alanine methyl ester

To a solution of N-butyloxycarbonyl-3-cyano-D-alanine (20.5 g, 97 mmol) and 4-dimethylaminopyridine (11.85 g, 97 mmol) in 150 mL THF and 33 mL methanol was added N,N'-dicyclohexylcarbodiimide (20 g, 97 mmol) and the solution was allowed to stir at room temperature for 2 hours. Insoluble material was removed by filtration and the solution was concentrated. The residue was taken up in ethyl acetate and the solution was washed with 5% citric acid, brine, NaHCO$_3$ and brine, dried (MgSO$_4$), and concentrated. Crystallization from ethyl acetate gave 18.8 g (85%) product. $^1$H-NMR: d (CDCl$_3$) 5.48 (d, 1H); 4.54 (m, 1H); 3.84 (s, 3H); 2.98 (m, 2H); 1.44 (s, 9H). ES-MS: calcd M+1 229.2; found 229.0.

(c) Methyl 4-amino-2(R)-(N-butyloxycarbonylamino)butyrate hydrochloride

N-Butyloxycarbonyl-3-cyano-D-alanine methyl ester (10.0 g, 43.85 mmol) was dissolved in 50 mL methanol and the solution was cooled in an ice bath. To it was added 50 mL methanol containing 6.9 mL 4N HCl in dioxane. The mixture was hydrogenated at 55 psi for 1 hour using PtO$_2$ as the catalyst. The catalyst was filtered and the solution was concentrated. The residue was triturated with ether to give 10.85 g (92%) product. $^1$H-NMR: d (DMSO-d$_6$) 8.10 (b, 3H); 7.42 (d, 1H); 4.10 (m, 1H); 3.64 (s, 3H); 2.80 (m, 2H); 1.95 (m, 2H); 1.38 (s, 9H). ES-MS: calcd M+1 233.2; found 233.0.

(d) Methyl 2(R)-(N-butyloxycarbonylamino)-4-(p-toluenesulfonylamino)butyrate

To a solution of methyl 4-amino-2(R)-(N-butyloxycarbonylamino)butyrate hydrochloride (2.28 g, 8.5 mmol) and p-toluenesulfonyl chloride (1.62 g, 8.5 mmol) in 10 mL CHCl3 cooled in an ice bath was added diisopropylethylamine (4.5 mL, 26 mmol). The mixture was stirred at room temperature overnight and concentrated. Ethyl acetate was added and the solution was washed with citric acid, brine, NaHCO$_3$ and brine, dried (MgSO$_4$) and concentrated. Purification on a silica gel column using 40% ethyl acetate/hexane gave 2.16 g (66%) product. $^1$H-NMR: d (CDCl$_3$) 7.75 (d, 2H ); 7.26 (d, 2H); 5.72 (t, 1H); 5.22 (d, 1H); 4.32 (m, 1H); 3.72 (s, 3H); 3.18 (m, 1H); 2.82 (m, 1H); 2.41 (s, 3H); 2.10 (m, 1H); 1.60 (m, 1H); 1.40 (s, 9H).

(e) Methyl 2(R)-amino-4-(p-toluenesulfonylamino)butyrate hydrochloride

Methyl 2(R)-(N-butyloxycarbonylamino)-4-(p-toluenesulfonylamino)butyrate (2.0 g, 5.18 mmol) was dissolved in 10 mL 4N HCl in dioxane and the solution was stirred for 1 hour and then concentrated. The residue was triturated with ether to give 1.16 g (70%) product. ES-MS: calcd M+1 287.2; found 287.0.

(f) Methyl 21(R)-(1(S)-benzyloxycarbonyl-3-phenylpropylamino)-4-(p-toluenesulfonylamino)butyrate To a solution of benzyl 2(R)-hydroxy-4-phenylbutyrate (3.0 g, 11.1 mmol) and 2,6-lutidine (1.9 g, 17.7 mmol) in 5 mL CH2Cl2 cooled in an ice bath was added trifluoromethanesilfonic anhydride (4.7 g, 16.6 mmol) and the solution was allowed to stir in the ice bath for 4 hours. Ethyl acetate was added and the solution was washed with citric acid, brine, NaHCO$_3$ and brine, dried (MgSO$_4$), and concentrated to give 3.97 g product.

The above compound (1.6 g, 4 mmol) was added to a solution of Methyl 2(R)-amino-4-(p-toluenesulfonylamino)butyrate hydrochloride in 3 mL CH$_2$Cl$_2$ cooled in an ice bath followed by diisopropylethylamine (1.4 mL, 8 mmol). After stirring overnight, the solution was concentrated. Purification on a silica gel column using 30% ethyl acetate/hexane as eluent gave 2.14 g (99%) product. ES-MS: calcd M+1 539.3; found 539.0.

(g) Methyl 2(R)-(1(S)-carboxy-3-phenylpropylamino)-4-(p-toluenesulfonylamino)butyrate Methyl 1(R)-(1(S)-benzyloxycarbonyl-3-phenylpropylamino)-4-(p-toluenesulfonylamino)butyrate (2.12 g, 3.7 mmol) was hydrogenated at atmospheric pressure for 1 hour in 10 mL isopropanol containing 0.1 mL 4N HCl in dioxane using 10% Pd/C as the catalyst. The catalyst was removed by filtration and the solution was concentrated to give 1.7 g (100%) product. ES-MS: calcd M+1 449.2; found (h) Methyl 2(R)-{1(S)-[1(S)-(2-benzimidazole)-2-methylpropylaminocarbonyl]-3-phenylpropylamino}-4-(p-toluenesulfonylamino)butyrate Methyl 1(R)-(1(S)-carboxy-3-phenylpropylamino)-4-(p-toluenesulfonylamino)butyrate (84 mg, 0.15 mmol) and 1-(2-benzimidazole)-2-methylpropylamine HCl salt (34 mg, 0.15 mmol) were dissolved in 1 mL DMF and the solution was cooled in an ice bath. To it was added TBTU (48 mg, 0.15 mmol) followed by diisopropylethylamine (0.08 mL, 0.45 mmol). After stirring for 2 hours, ethyl acetate was added and the solution was washed with NaHCO$_3$ and brine, dried (MgSO$_4$) and concentrated. Purification on a silica gel column gave 91 mg (98%) product. ES-MS: calcd M+1 620.3; found 620.4.

(i) 2(R)-{1(S)-[1(S)-(2-benzimidazole)-2-methylpropylaminocarbonyl]-3-phenylpropylamino}-3-(p-toluenesulfonylamino)butyric acid Methyl 1(R)-{1(S)-[1(S)-(2-benzimidazole)-2-methylpropylaminocarbonyl]-3-phenylpropylamino}-4-(p-toluenesulfonylamino)butyrate (90 mg, 0.14 mmol) was dissolved in 2 mL THF and 0.4 mL of 1N LiOH was added. After stirring 1 hour, the solution was acidified with HCl to pH 3. Purification on HPLC gave 55 mg (55%) product. ES-MS: cacld M+1 606.3; found 606.3.

Example 301

1(R)-{1(S)-[1(S)-(2-Benzimidazole)-2-phenylethylaminocarbonyl]-3-phenylpropylamino}-3-(p-toluenesulfonylamino)butyric acid:

This compound was prepared in a manner analogous to that described in Example 300. ES-MS: calcd M+1 654.3; found 654.3.

Example 302

1(R)-{1(S)-[1(S)-(2-Benzimidazole)ethylaminocarbonyl]-3-phenylpropylamino}-3-(p-toluenesulfonylamino)butyric acid:

This compound was prepared in a manner analogous to that described in Example 300. ES-MS: calcd M+1 578.3; found 578.4.

Example 303

1(R)-{1(S)-[1(S)-(2-Benzimidazole)-3-methylbutylaminocarbonyl]-3-phenylpropylamino}-3-(p-toluenesulfonylamino)butyric acid:

This compound was prepared in a manner analogous to that described in Example 300. ES-MS: calcd M+1 620.3; found 620.4.

Example 304

1(R)-{1(S)-[1(S)-(2-Benzimidazole)-2-methylbutylaminocarbonyl]-3-phenylpropylamino}-3-(p-toluenesulfonylamino)butyric acid:

This compound was prepared in a manner analogous to that described in Example 300. ES-MS: calcd M+1 620.3; found 620.3.

Example 425

2(R)-n-butyl-4-(2-(1,1'-biphenylethyl)-4-[1S-(2-imidazole)neopentylaminocarbonyl]butyric acid trifluoroacetate 1-oxa-2-oxo-5-phenyl(4-phenyl)cyclopentane A titanium homoenolate solution was prepared as follows.

To a stirred solution of ehtyl 3-iodopropanoate (2.12 g, 9.32 mmol) in 15 ml anhydrous toluene and 1.58 ml of freshly distilled N,N-dimethyl acetamide, was added 0.98 g of Zn-Cu complex. The mixture was heated to 80° C. for 4 h.

To a separate flask conatining TiOiPr$_4$ (2.06 ml) in 2 ml CH$_2$Cl$_2$, was added dropwise TiCl$_4$(2.33 ml, 1M). The mixture was stirred 15 min then cooled to −40. The cooled ZnCu complex above (RT) was then cannulated into the TiCl$_2$OiPr$_2$ solution and the mixture allowed to stir at −20 for 20 min and then recooled to −40° C.

4-phenylbenzaldehyde (1.36 g, 7.46 mmol) in 10 ml CH$_2$Cl$_2$ was added dropwise to the above, and stirred for 15 min at −40 then allowed to reach room temperature over 18 h. The mixture was worked up by pouring into a mixture of 10% HCl and ether and stirred for 10 min. The solution was then extracted with ethyl acetate, washed with water, brine, then dried over MgSO$_4$. Following filtration the crude material was recrystallized from ethyl acetate hexane to afford 1.42 g (80%) pure material. MP 103.5°–104° C.; EIMS (M+H) 239; IR (KBr) 1766 cm$^{-1}$.

4-Biphenyl Butanoic Acid

To the lactone above (1.06 g, 4.5 mmol) in 20 ml MeOH and 10 ml ethyl acetate, was added 0.10 g 10% Pd-C. The solution was treated with H$_2$ at 1 atm for 1.5 h. The solution was then filtered and evaporated to give 1.0 g (94%) of acid. MP 119.5°–120.5° C.; CIMS (M+NH$_4^+$) 258; IR (KBr) 1696, 3026 cm$^{-1}$.

Prepared as described previously to give a 74% yield.
Michael Addition Product (WO 94/12169)

To a stirred solution of TiCl$_4$ (1.88 ml, 1M) in 9 ml of CH$_2$Cl$_2$ at 0° C., was added 0.9 ml TiOiPr$_4$ dropwise over 15 min, followed by 0.44 ml of diisopropylethylamine. After an additional 20 min, the above (0.95 g, 2.38 mmol) was added in one portion and allowed to stir for 1 h at 0° C. Tert-butyl acrylate (0.52 ml, 3.57 mmol) was added, and the cooling bath was removed, followed by stirring at RT for 12 h. The reaction was quenched with NH$_4$Cl (sat), the aqueous layer was separated and extracted additionaly with CH$_2$Cl$_2$. The combined organics were then washed again with NH$_4$Cl, water and brine. The solution was dried with MgSO$_4$, filtered and evaporated to give a crude oil which was purified by MPLC (25% ethyl acetate/hexane). 0.886 g of pure material was isolated.

Removal of Chiral Auxiliary

To a solution of the above (5.71 g, 10.8 mmol) in 67 ml THF/17 ml water cooled to 0° C. was added a mixture 8.8 ml of 30% H$_2$O$_2$ 43.3 mmol of LiOH. The solution was evaporated after 1.5 h, and the resulting material acidified with 10% citric acid. The organic material was extracted with ethyl acetate, washed with water and brine and dried over MgSO$_4$. Filtration and removal of solvent gave a slurry containing the oxazolidinone and crude acid. Addition of ether and a seed crystal of S-4-(phenylmethyl)oxazolidinone followed by cooling to −20, gave a solid precipitate which was removed by filtration. The product acid was further purified by making a dicylohexylamine salt and recrystalizing from ether. The acid was then free based using 5% KHSO$_4$ to give the acid as a crystailne product that could be used without further purification in the next step.

Alkylation Reaction

To a stirred cooled (−78° C.) solution of the acid (1.01 g, 2.73 mmol) in 20 ml THF/5 ml DMPU, was added LDA (5.46 ml, 1M) over 10 min. Following addition the solution was allowed to stir for 1 h at −40° C. Butyl iodide (0.31 ml, 2.73 mmol) was added, and the solution allowed to gradually reach room temp over 12 h. The crude material was then poured into 10% citric acid and extracted with ethyl acetate. The combined organics were washed with water, brine and then dried over MgSO$_4$. Filtration and removal of the solvent, gave the desired product as 4:1 mixture of diastereomers [could be separated directly by SiO$_2$ HPLC or purified via making the benzyl ester and MPLC purification as per WO 94/12169].

The acid was coupled with the above as described previously, with 1-(2-imidazole)-2,2-dimethylpropyl amine, followed by removal of the t-butyl group with TFA to give the title compound example 425; MS 537; MP 174° C.

TABLE 1

$$\text{HONH-C(=O)-C(R^1)(R^{1a})-CH(R^2)-C(=O)-NH-CH(R^3)-Q}$$

| Ex. No. | R¹ | R¹ᵃ | R² | R³ | Q |
|---|---|---|---|---|---|
| 1 | H | H | isobutyl | 1-naphthyl | 5-azabenzimidazol-2-yl |
| 2 | H | H | isobutyl | 2-naphthyl | 5-azabenzimidazol-2-yl |
| 3 | H | H | isobutyl | cyclohexylmethyl | 5-azabenzimidazol-2-yl |
| 4 | H | H | isobutyl | benzyl | 5-chloro-2-benzimidazolyl |
| 5 | H | H | isobutyl | t-butyl | 5-chloro-2-benzimidazolyl |
| 6 | H | H | isobutyl | neopentyl | 5-chloro-2-benzimidazolyl |
| 7 | H | H | isobutyl | isobutyl | 5-chloro-2-benzimidazolyl |
| 8 | H | H | isobutyl | 2-naphthyl | 5-chloro-2-benzimidazolyl |
| 9 | H | H | isobutyl | 1-naphthyl | 5-chloro-2-benzimidazolyl |
| 10 | H | H | isobutyl | cyclohexylmethyl | 5-chloro-2-benzimidazolyl |
| 11 | H | H | isobutyl | benzyl | 4,6-dichloro-2-benzimidazolyl |
| 12 | H | H | isobutyl | t-butyl | 4,6-dichloro-2-benzimidazolyl |
| 13 | H | H | isobutyl | neopentyl | 4,6-dichloro-2-benzimidazolyl |
| 14 | H | H | isobutyl | isobutyl | 4,6-dichloro-2-benzimidazolyl |
| 15 | H | H | isobutyl | 2-naphthyl | 4,6-dichloro-2-benzimidazolyl |
| 16 | H | H | isobutyl | 1-naphthyl | 4,6-dichloro-2-benzimidazolyl |
| 17 | H | H | isobutyl | cyclohexylmethyl | 4,6-dichloro-2-benzimidazolyl |
| 18 | H | H | isobutyl | benzyl | 5-fluoro-2-benzimidazolyl |
| 19 | H | H | isobutyl | neopentyl | 5-fluoro-2-benzimidazolyl |
| 20 | H | H | isobutyl | isobutyl | 5-fluoro-2-benzimidazolyl |
| 21 | H | H | isobutyl | 1-naphthyl | 5-fluoro-2-benzimidazolyl |
| 22 | H | H | isobutyl | cyclohexylmethyl | 5-fluoro-2-benzimidazolyl |
| 23 | H | H | isobutyl | t-butyl | 5-fluoro-2-benzimidazolyl |
| 24 | H | H | isobutyl | 2-naphthyl | 2-imidazolyl |
| 25 | H | H | isobutyl | cyclohexylmethyl | 2-imidazolyl |
| 26 | H | H | isobutyl | 1-naphthyl | 2-imidazolyl |
| 27 | H | H | isobutyl | 2-naphthyl | 2-thiazolyl |
| 28 | H | H | isobutyl | 1-naphthyl | 2-thiazolyl |
| 29 | H | H | phenpropyl | 4-aminobutyl | 2-thiazolyl |
| 30 | H | H | phenpropyl | isobutyl | 2-thiazolyl |
| 31 | H | H | phenpropyl | cyclohexylmethyl | 2-thiazolyl |
| 32 | H | H | phenpropyl | benzyl | 2-thiazolyl |
| 33 | CH₃ | H | isobutyl | isobutyl | 5-methoxy-2-benzimidazolyl |
| 34 | CH₃ | H | isobutyl | t-butyl | 5-methoxy-2-benzimidazolyl |
| 35 | CH₃ | H | isobutyl | 2-naphthyl | 5-methoxy-2-benzimidazolyl |
| 36 | CH₃ | H | isobutyl | cyclohexylmethyl | 5-methoxy-2-benzimidazolyl |
| 37 | CH₃ | H | isobutyl | neopentyl | 5-methoxy-2-benzimidazolyl |
| 38 | CH₃ | H | isobutyl | 1-naphthyl | 5-methoxy-2-benzimidazolyl |
| 39 | CH₃ | H | isobutyl | 2-naphthyl | 5-azabenzimidazol-2-yl |
| 40 | CH₃ | H | isobutyl | cyclohexylmethyl | 5-azabenzimidazol-2-yl |
| 41 | CH₃ | H | isobutyl | 1-naphthyl | 5-azabenzimidazol-2-yl |
| 42 | CH₃ | H | isobutyl | benzyl | 2-thiazolyl |
| 43 | CH₃ | H | isobutyl | isobutyl | 2-thiazolyl |
| 44 | CH₃ | H | isobutyl | t-butyl | 2-thiazolyl |
| 45 | CH₃ | H | isobutyl | 2-naphthyl | 2-thiazolyl |
| 46 | CH₃ | H | isobutyl | cyclohexylmethyl | 2-thiazolyl |
| 47 | CH₃ | H | isobutyl | 3-indolyl | 2-thiazolyl |
| 48 | CH₃ | H | isobutyl | 1-naphthyl | 2-thiazolyl |
| 49 | phen propyl | H | isobutyl | 2-naphthyl | 5-azabenzimidazol-2-yl |
| 50 | phen propyl | H | isobutyl | 1-naphthyl | 5-azabenzimidazol-2-yl |
| 51 | —(CH₂)₃—2-pyridine | H | isobutyl | 2-naphthyl | 5-azabenzimidazol-2-yl |
| 52 | —(CH₂)₃—2-pyridine | H | isobutyl | 1-naphthyl | 5-azabenzimidazol-2-yl |
| 53 | —(CH₂)₃—1-pyrazole | H | isobutyl | 2-naphthyl | 5-azabenzimidazol-2-yl |
| 54 | —(CH₂)₃—1-pyrazole | H | isobutyl | 1-naphthyl | 5-azabenzimidazol-2-yl |
| 55 | —(CH₂)₃—1-pyrazole | H | isobutyl | 2-naphthyl | 5-azabenzimidazol-2-yl |
| 56 | —(CH₂)₃—1-pyrazole | H | isobutyl | 1-naphthyl | 5-azabenzimidazol-2-yl |
| 57 | 2-fluoro benzyl | H | isobutyl | 2-naphthyl | 5-azabenzimidazol-2-yl |
| 58 | 2-fluoro benzyl | H | isobutyl | 1-naphthyl | 5-azabenzimidazol-2-yl |
| 59 | 3-fluoro benzyl | H | isobutyl | 2-naphthyl | 5-azabenzimidazol-2-yl |
| 60 | 3-fluoro benzyl | H | isobutyl | 1-naphthyl | 5-azabenzimidazol-2-yl |
| 61 | 4-fluoro benzyl | H | isobutyl | 2-naphthyl | 5-azabenzimidazol-2-yl |
| 62 | 4-fluoro benzyl | H | isobutyl | 1-naphthyl | 5-azabenzimidazol-2-yl |
| 63 | allyl | H | isobutyl | 2-naphthyl | 5-azabenzimidazol-2-yl |
| 64 | allyl | H | isobutyl | cyclohexylmethyl | 5-azabenzimidazol-2-yl |
| 65 | allyl | H | isobutyl | 1-naphthyl | 5-azabenzimidazol-2-yl |
| 66 | CH₃ | H | isobutyl | 2-naphthyl | 2-imidazolyl |
| 67 | CH₃ | H | isobutyl | cyclohexylmethyl | 2-imidazolyl |
| 68 | CH₃ | H | isobutyl | 1-naphthyl | 2-imidazolyl |
| 69 | CH₃ | H | phenpropyl | benzyl | 5-methylisoxazolin--3-yl |

TABLE 1-continued

HONH-C(=O)-C(R¹)(R¹ᵃ)-CH(R²)-C(=O)-NH-CH(R³)-Q

| Ex. No. | R¹ | R¹ᵃ | R² | R³ | Q |
|---|---|---|---|---|---|
| 70 | CH₃ | H | phenpropyl | cyclohexylmethyl | 5-methylisoxazolin--3-yl |
| 71 | CH₃ | H | phenpropyl | 4-aminobutyl | 5-methylisoxazolin--3-yl |
| 72 | propargyl | H | isobutyl | 2-naphthyl | 5-azabenzimidazol-2-yl |
| 73 | propargyl | H | isobutyl | cyclohexylmethyl | 5-azabenzimidazol-2-yl |
| 74 | propargyl | H | isobutyl | 1-naphthyl | 5-azabenzimidazol-2-yl |
| 75 | OH | H | isobutyl | 2-naphthyl | 5-azabenzimidazol-2-yl |
| 76 | OH | H | isobutyl | cyclohexylmethyl | 5-azabenzimidazol-2-yl |
| 77 | OH | H | isobutyl | benzyl | 5-methoxy-2-benzimidazolyl |
| 78 | OH | H | isobutyl | isobutyl | 5-methoxy-2-benzimidazolyl |
| 79 | OH | H | isobutyl | t-butyl | 5-methoxy-2-benzimidazolyl |
| 80 | OH | H | isobutyl | 2-naphthyl | 5-methoxy-2-benzimidazolyl |
| 81 | OH | H | isobutyl | cyclohexylmethyl | 5-methoxy-2-benzimidazolyl |
| 82 | OH | H | isobutyl | neopentyl | 5-methoxy-2-benzimidazolyl |
| 83 | GH | H | isobutyl | 1-naphthyl | 5-methoxy-2-benzimidazolyl |
| 84 | OH | H | isobutyl | benzyl | 5-chloro-2-benzimidazolyl |
| 8S | OH | H | isobutyl | isobutyl | 5-chloro-2-benzimidazolyl |
| 86 | OH | H | isobutyl | t-butyl | 5-chloro-2-benzimidazolyl |
| 87 | OH | H | isobutyl | 2-naphthyl | 5-chloro-2-benzimidazolyl |
| 88 | OH | H | isobutyl | cyclohexylmethyl | 5-chloro-2-benzimidazolyl |
| 89 | OH | H | isobutyl | neopentyl | 5-chloro-2-benzimidazolyl |
| 90 | OH | H | isobutyl | 1-naphthyl | 5-chloro-2-benzimidazolyl |
| 91 | benzyloxy | H | isobutyl | 2-naphthyl | 5-azabenzimidazol-2-yl |
| 92 | benzyloxy | H | isobutyl | 1-naphthyl | 5-azabenzimidazol-2-yl |
| 93 | 2-picolyloxy | H | isobUtyl | 2-naphthyl | 5-azabenzimidazol-2-yl |
| 94 | 3-picolyloxy | H | isobutyl | 1-naphthyl | 5-azabenzimidazol-2-yl |
| 95 | 4-picolyloxy | H | isobutyl | 2-naphthyl | 5-azabenzimidazol-2-yl |
| 96 | 4-picolyloxy | H | isobutyl | 1-naphthyl | s-azabenzimidazol-2-yl |
| 97 | allyloxy | H | isobutyl | 2-naphthyl | 5-azabenzimidazol-2-yl |
| 98 | allyloxy | H | isobutyl | 1-naphthyl | 5-azabenzimidazol-2-yl |
| 99 | propargyloxy | H | isobutyl | 2-naphthyl | 5-azabenzimidazol-2-yl |
| 100 | propargyloxy | H | isobutyl | 1-naphthyl | 5-azabenzimidazol-2-yl |
| 101 | OH | H | phenpropyl | isobutyl | 2-thiazolyl |
| 102 | OH | H | phenpropyl | cyclohexylmethyl | 2-thiazolyl |
| 103 | OH | H | phenpropyl | benzyl | 2-thiazolyl |
| 104 | OH | H | phenpropyl | 4-aminobutyl | 2-thiazolyl |
| 105 | OH | H | isobutyl | 2-naphthyl | 2-imidazolyl |
| 106 | OH | H | isobutyl | cyclohexylmethyl | 2-imidazolyl |
| 107 | OH | H | isobutyl | 1-naphthyl | 2-imidazolyl |
| 108 | OH | H | phenpropyl | benzyl | 5-methylisoxazolin-3-yl |
| 109 | OH | H | phenpropyl | cyclohexylmethyl | 5-methylisoxazolin-3-yl |
| 110 | OH | H | phenpropyl | 4-aminobutyl | 5-methylisoxazolin-3-yl |
| 111 | benzyloxy | H | isobutyl | 2-naphthyl | 2-imidazolyl |
| 112 | benzyloxy | H | isobutyl | 1-naphthyl | 2-imidazolyl |
| 113 | allyloxy | H | isobutyl | 2-naphthyl | 2-imidazolyl |
| 114 | allyloxy | H | isobutyl | 1-naphthyl | 2-imidazolyl |
| 115 | propargyloxy | H | isobutyl | 2-naphthyl | 2-imidazolyl |
| 116 | propargyloxy | H | isobutyl | 1-naphthyl | 2-imidazolyl |
| 117 | 3-picolyloxy | H | isobutyl | 2-naphthyl | 2-imidazolyl |
| 115 | 3-picolyloxy | H | isobutyl | 1-naphthyl | 2-imidazolyl |
| 119 | CH₃ | OH | isobutyl | 2-naphthyl | 5-azabenzimidazol-2-yl |
| 120 | CH₃ | OH | isobutyl | 1-naphthyl | 5-azabenzimidazol-2-yl |
| 121 | CH₃ | OH | isobutyl | 2-naphthyl | 5-chloro-2-benzimidazolyl |
| 122 | CH₃ | OH | isobutyl | cyclohexylmethyl | 5-chloro-2-benzimidazolyl |
| 123 | CH₃ | OH | isobutyl | 1-naphthyl | 5-chloro-2-benzimidazolyl |
| 124 | CH₃ | OH | phenpropyl | benzyl | 5-methylisoxazolin-3-yl |
| 125 | CH₃ | OH | phenpropyl | isobutyl | 5-methylisoxazolin-3-yl |
| 126 | CH₃ | OH | phenpropyl | t-butyl | 5-methylisoxazolin-3-yl |
| 127 | CH₃ | OH | phenpropyl | 4-aminobutyl | 5-methylisoxazolin-3-yl |
| 128 | CH₃ | OH | phenpropyl | cyclohexylmethyl | 5-methylisoxazolin-3-yl |
| 129 | CH₃ | OH | phenpropyl | neopentyl | 5-methylisoxazolin-3-yl |
| 130 | CH₃ | OH | phenpropyl | 3-indolyl | 5-methylisoxazolin-3-yl |
| 131 | CH₃ | OH | phenpropyl | benzyl | 2-thiazolyl |
| 132 | CH₃ | OH | phenpropyl | isobutyl | 2-thiazolyl |
| 133 | CH₃ | OH | phenpropyl | t-butyl | 2-thiazolyl |
| 134 | CH₃ | OH | phenpropyl | 3-indolyl | 2-thiazolyl |
| 135 | CH₃ | OH | phenpropyl | cyclohexyl methyl | 2-thiazolyl |
| 136 | CH₃ | OH | phenpropyl | neopentyl | 2-thiazolyl |
| 137 | CH₃ | OH | phenpropyl | 4-aminobutyl | 2-thiazolyl |
| 139 | CH₃ | OH | phenpropyl | benzyl | 2-oxazolyl |

TABLE 1-continued

| Ex. No. | R¹ | R¹ᵃ | R² | R³ | Q |
|---|---|---|---|---|---|
| 139 | $CH_3$ | OH | phenpropyl | cyclohexyl methyl | 2-oxazolyl |
| 140 | $CH_3$ | OH | phenpropyl | isobutyl | 2-oxazolyl |
| 141 | $CH_3$ | OH | phenpropyl | 4-aminobutyl | 2-oxazolyl |
| 142 | $CH_3$ | OH | phenpropyl | 3-indolyl | 2-oxazolyl |
| 143 | $CH_3$ | OH | phenpropyl | neopentyl | 2-oxazolyl |
| 144 | $CH_3$ | H | isobutylpyl | phenyl | phenyl |
| 14S | $CH_3$ | H | phenethyl | phenyl | phenyl |
| 146 | $CH_3$ | H | biphenylethyl | phenyl | phenyl |

TABLE 2

| Ex. No. | R⁹ | R⁹ᵃ | R² | R³ | Q |
|---|---|---|---|---|---|
| 300 | p-toluenesulfonylamino ethyl | H | phenethyl | benzyl | 2-benzimidazolyl |
| 301 | p-toluenesulfonylamino ethyl | H | phenethyl | isopropyl | 2-benzimidazolyl |
| 302 | p-toluenesulfonylamino ethyl | H | phenethyl | methyl | 2-benzimidazolyl |
| 303 | p-toluenesulfonylamino ethyl | H | phenethyl | isobutyl | 2-benzimidazolyl |
| 304 | p-toluenesulfonylamino ethyl | H | phenethyl | 2-butyl | 2-benzimidazolyl |
| 305 | phthalimido butyl | H | phenethyl | benzyl | 2-thiazolyl |
| 306 | phthalimido butyl | H | phenethyl | isobutyl | 2-thiazolyl |
| 307 | phthalimido butyl | H | phenethyl | benzyl | 5-azabenzimidazol-2-yl |
| 308 | phthalimido butyl | H | phenethyl | isobutyl | 5-azabenzimidazol-2-yl |
| 309 | phthalimido butyl | H | phenethyl | 2-naphthyl | 5-azabenzimidazol-2-yl |
| 310 | phthalimido butyl | H | phenethyl | 1-naphthyl | 5-azabenzimidazol-2-yl |
| 311 | phthalimido butyl | H | phenethyl | benzyl | 2-imidazolyl |
| 312 | phthalimido butyl | H | phenethyl | isobutyl | 2-imidazolyl |
| 313 | phthalimido butyl | H | phenethyl | benzyl | 5-methylisoxazolin-3-yl |
| 314 | phthalimido butyl | H | phenethyl | isobutyl | 5-methylisoxazolin-3-yl |
| 315 | phthalimido butyl | H | phenethyl | 4-aminobutyl | 5-methylisoxazolin-3-yl |
| 316 | triethyl | H | biphenylethyl | benzyl | 2-benzimidazolyl |
| 317 | methyl | H | biphenylethyl | isobutyl | 2-benzimidazolyl |
| 318 | methyl | H | biphenylethyl | benzyl | 2-thiazolyl |
| 319 | methyl | H | biphenylethyl | isobutyl | 2-thiazolyl |
| 320 | methyl | H | biphenylethyl | benzyl | 2-oxazolyl |
| 321 | methyl | H | biphenylethyl | isobutyl | 2-oxazolyl |
| 322 | methyl | H | biphenylethyl | benzyl | 5-azabenzimidazol-2-yl |
| 323 | methyl | H | biphenylethyl | isobutyl | 5-azabenzimidazol-2-yl |
| 324 | methyl | H | biphenylethyl | benzyl | 2-imidazolyl |
| 325 | methyl | H | biphenylethyl | isobutyl | 2-imidazolyl |
| 326 | methyl | H | biphenylethyl | benzyl | 4-chloro-2-imidazolyl |
| 327 | methyl | H | biphenylethyl | isobutyl | 4-chloro-2-imidazolyl |
| 328 | methyl | H | biphenylethyl | 2-naphthyl | 2-imidazolyl |
| 329 | methyl | H | biphenylethyl | 1-naphthyl | 2-imidazolyl |

TABLE 3

Structure: HO-C(=O)-C(R⁹)(R⁹ᵃ)-CH(R²)-C(=O)-NH-CH(R³)-C(=O)-Q

| Ex. No. | $R^9$ | $R^{9a}$ | $R^2$ | $R^3$ | Q |
|---|---|---|---|---|---|
| 400 | Me | H | 2-(1,1'-biphenyl)ylethyl | benzyl | 2-benzimidazolyl |
| 401 | Me | H | 2-(1,1'-biphenyl)ylethyl | isobutyl | 2-benzimidazolyl |
| 402 | Me | H | 2-(1,1'-biphenyl)ylethyl | benzyl | 2-imidazolyl |
| 403 | Me | H | 2-(1,1'-biphenyl)ylethyl | isobutyl | 2-imidazolyl |
| 404 | Me | H | 2-(1,1'-biphenyl)ylethyl | phenyl | phenyl |
| 405 | n-Bu | H | 2-(1,1'-biphenyl)ylethyl | benzyl | 2-benzimidazolyl |
| 406 | n-Bu | H | 2-(1,1'-biphenyl)ylethyl | isobutyl | 2-benzimidazolyl |
| 407 | n-Bu | H | 2-(1,1'-biphenyl)ylethyl | benzyl | 2-imidazolyl |
| 408 | n-Bu | H | 2-(1,1'-biphenyl)ylethyl | isobutyl | 2-imidazolyl |
| 409 | n-Bu | H | 2-(1,1'-biphenyl)ylethyl | phenyl | phenyl |
| 410 | n-Bu | H | 2-(1,1'-biphenyl)ylpropyl | benzyl | 2-benzimidazolyl |
| 411 | n-Bu | H | 2-(1,1'-biphenyl)ylpropyl | isobutyl | 2-benzimidazolyl |
| 412 | n-Bu | H | 2-(1,1'-biphenyl)ylpropyl | benzyl | 2-imidazolyl |
| 413 | n-Bu | H | 2-(1,1'-biphenyl)ylpropyl | isobutyl | 2-imidazolyl |
| 414 | n-Bu | H | 2-(1,1'-biphenyl)ylpropyl | phenyl | phenyl |
| 415 | n-Bu | H | 2-[(4-t-butyl)phenyl]ethyl | benzyl | 2-benzimidazolyl |
| 416 | n-Bu | H | 2-[(4-t-butyl)phenyl]ethyl | isobutyl | 2-benzimidazolyl |
| 417 | n-Bu | H | 2-[(4-t-butyl)phenyl]ethyl | benzyl | 2-imidazolyl |
| 418 | n-Bu | H | 2-[(4-t-butyl)phenyl]ethyl | isobutyl | 2-imidazolyl |
| 419 | n-Bu | H | 2-[(4-t-butyl)phenyl]ethyl | phenyl | phenyl |
| 420 | Me | H | n-octyl | benzyl | 2-benzimidazolyl |
| 421 | Me | H | n-octyl | isobutyl | 2-benzimidazolyl |
| 422 | Me | H | n-octyl | benzyl | 2-imidazolyl |
| 423 | Me | H | n-octyl | isobutyl | 2-imidazolyl |
| 424 | Me | H | n-octyl | phenyl | phenyl |
| 425 | Butyl | H | 2-(1,1-biphenyl)ylethyl) | tert-butyl | 2-imidazolyl |

Utility

The compounds of formula I possess matrix metalloproteinase and/or TNF inhibitory activity. The MMP-3 inhibitory activity of the compounds of the present invention is demonstrated using assays of MMP-3 activity, for example, using the assay described below for assaying inhibitors of MMP-3 activity. The compounds of the present invention are bioavailable in vivo as demonstrated, for example, using the ex vivo assay described below. The compounds of formula I have the ability to suppress/inhibit cartilage degradation in vivo, for example, as demonstrated using the animal model of acute cartilage degradation described below.

The compounds provided by this invention are also useful as standards and reagents in determining the ability of a potential pharmaceutical to inhibit MMP-3. These would be provided in commercial kits comprising a compound of this invention.

Matrixmetalloproteinases have also been implicated in the degradation of basement membranes to allow infiltration of cancer cells into the circulation and subsequent penetration into other tissues leading to tumor metastasis. (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention would also have utility for the prevention and treatment of osteopenia associated with matrixmetalloproteinase-mediated breakdown of cartilage and bone which occurs in osteoporosis patients.

Compounds which inhibit the production or action of TNF and/or MMP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, osteo and rheumatoid arthritis, multiple sclerosis, radiation damage, and hyperoxic alveolar injury.

The compounds of the present invention have been shown to inhibit TNF production in lipopolysacharride stimulated mice, for example, using the assay for TNF Induction in Mice described below.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of MMP-3.

Bisacetylated Substance P/MMP-3 Fluorescent Assay

A high capacity enzymatic assay was developed to detect potential inhibitors of MMP-3. The assay uses a derivative of a peptide substrate, substance P (Arg-Pro-Lys-Pro-Gln-Gln-Phe-Phe-Gly-Leu-Met), which is cleaved by MMP-3 exclusively at the glutamine-phenylalanine bond. In order to adapt this assay for high throughput screening, we have developed a fluorimetric method of product detection. The production of the hydrolysis product, substance P 7–11, is measured by reaction with fluorescamine, a fluorogenic compound which reacts with the primary amine of this fragment. The substance P substrate is bisacetylated to block the primary amines of the intact substrate. Thus, the resulting fluorescence represents generation of product (7–11 peptide) formed upon cleavage by MMP-3, and is quantitated using a standard curve prepared with known concentrations of 7–11 peptide. Kinetic studies using the bisacetylated substrate yield the following parameters for MMP-3: Km=769±52 uM; Vmax=0.090±0.003 nmoles 7–11 peptide/min.

To evaluate inhibition of MMP-3, compounds were prepared at a concentration of 10 mM in 100% methanol, and then further diluted to a 20× molar stock. Five microliters of each drug stock was added to the assay in the presence of 20 nM truncated MMP-3 in 67.5 mM tricine (pH 7.5), 10 mM $CaCl_2$, 40 mM NaCl, and 0.005% Brij 35 in a final volume of 100 microliters. Bisacetylated substance P (1000 mM) was added, and the assay was run for 1 hour at 25° C. The reaction was quenched with EDTA (20 mM) and product was detected fluorometrically following addition of fluorescamine (0.075 mg/ml). Fluorescence of each sample was converted to an amount of product formed using a substance P 7–11 standard curve. Under these conditions, the assay is linear with respect to MMP-3 amount up to 10 pmoles. Inhibition of MMP-3 was determined by comparing the amount of product generated in the presence and absence of compound.

Selected compounds of the present invention were tested and shown to have activity in the above assay.

Ex Vivo Assay for Bioavailability of MMP-3 Inhibitors

Blood was collected by cardiac puncture from rats at different times after dosing I.V., I.P., or P.O. with compound in order to determine the levels of inhibitor present. Plasma was extracted with 10% TCA in 95% methanol, and placed on ice for 10 minutes. The plasma was then centrifuged for 15 minutes at 14,000 rpm in an Eppendorf microcentrifuge. The supernatant was removed, recentrifuged, and the resulting supernatant was diluted 1:10 in 50 mM tricine, pH 8.5. The pH of the sample was adjusted to 7.5, and then assayed in the MMP-3 substance P fluorescent enzymatic assay. Plasma from naive rats was extracted by the same method and used as a negative control. This plasma was also used to prepare a spiked plasma curve of the compound of interest. Known concentrations of the compound were added to control plasma, the plasma was extracted by the same method, and then assayed in the MMP-3 enzymatic assay. A standard curve was prepared that related percent inhbition in the MMP-3 assay to the concentration of drug added in the spiked samples. Based on the percent inhibition in the presence of plasma from dosed rats, the concentration of compound was determined using the standard curve.

Table B shows the results of dosing of representative compounds of the invention orally in rats at 100 mg/kg.

TABLE B

| Ex. No. | $C_{max}$ (µM/ml) |
|---------|-------------------|
| 86      | 0.96              |

TNF Induction in Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action, MMP-3, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 1.0 |
| Acacia | 4.7 |
| Sodium carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

The term "consisting essentially of" where used in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited references may provide further useful information, however, these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A compound of the formula I:

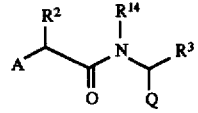

or pharmaceutically acceptable salts or prodrug forms thereof, wherein:

A is $-C(R^1)(R^{1a})CONHOH$;

Q is selected from:
  pyridyl substituted with 0–3 $R^5$, $R^6$, and/or $R^7$,
  triazole substituted with 0–3 $R^5$, $R^6$, and/or $R^7$,
  thiazole substituted with 0–3 $R^5$, $R^6$, and/or $R^7$,
  tetrazole substituted with 0–3 $R^5$, $R^6$, and/or $R^7$,
  oxazole substituted with 0–3 $R^5$, $R^6$, and/or $R^7$,
  isoxazole substituted with 0–3 $R^5$, $R^6$, and/or $R^7$,
  pyrazole substituted with 0–3 $R^5$, $R^6$, and/or $R^7$,
  thiopyrazole substituted with 0–3 $R^5$, $R^6$, and/or $R^7$,
  isoxazoline substituted with 0–3 $R^5$, $R^6$, and/or $R^7$,
  benzimidazole substituted with 1–3 $R^5$, $R^6$, and/or $R^7$, when at least one of $R^5$, $R^6$ or $R^7$ are other than H or $C_1$–$C_4$ alkyl,
  benzoxazole substituted with 0–3 $R^5$, $R^6$, and/or $R^7$,
  benzothiazole substituted with 0–3 $R^5$, $R^6$, and/or $R^7$,
  When $R^3$ is a cyclohexyl, cyclohexylmethyl, naphthyl, Q can also be a benzimidazole substituted with 0–3 $R^5$, $R^6$, and/or $R^7$, or an imidazole substituted with 0–3 $R^5$, $R^6$, and/or $R^7$, The phenyl ring of the benzimidazole, benzoxazole and benzothiazole can be optionally replaced with 1–2 nitrogens.

$R^1$ and $R^{1a}$ are independently selected from:
  H, halogen, $OR^{17}$, $NR^{10}R^{10a}$, $NR^8R^{10a}$, $S(O)_mR^{17a}$,
  $C_1$–$C_4$ alkyl substituted with 0–3 $R^4$,
  $C_2$–$C_4$ alkenyl substituted with 0–3 $R^4$,
  $C_2$–$C_4$ alkynyl substituted with 0–3 $R^4$,
  $C_6$–$C_{10}$ aryl substituted with 0–3 $R^{18}$,
  a $C_5$–$C_{11}$ heterocycle containing from 1–4 heteroatoms selected from N, O or S, said heterocycle optionally substituted with 0–3 $R^{18}$, or
  $C_3$–$C_8$ cycloalkyl, Alternately, $R^1$ and $R^{1a}$ can be taken together to form a 3–7 membered carbocyclic or heterocyclic, said heterocyclic ring containing from 1–2 heteroatoms selected from N, O or S;

$R^2$ is selected from:
  H
  $C_1$–$C_6$ alkyl substituted with 0–3 $R^{17b}$,
  $-O-(C_1-C_8$ alkyl$)-R^{20}$,
  $-S-(C_1-C_8$ alkyl$)-R^{20}$,
  $-CH_2O-(C_1-C_8$ alkyl$)-R^{20}$, or
  $-CH_2S-(C_1-C_8$ alkyl$)-R^{20}$;

$R^3$ is selected from:
  H,
  $C_1$–$C_6$ alkyl substituted with 0–3 $R^{17b}$,
  $-(C_1-C_6$ alkylene$)-OR^{12}$,
  $-(C_1-C_6$ alkylene$)-SR^{12}$,
  $C_6$–$C_{10}$ aryl substituted with 0–3 $R^{18}$, or
  $C_3$–$C_7$ cycloalkyl;

$R^4$ is selected from:
  $-OR^{17}$, $-SO_mR^{17}$,
  $-NR^8R^{10}$, $-NHC(=NR^8)N(R^8)R^{10}$,
  $C_1$–$C_4$ alkyl,
  aryl substituted with 0–5 $R^{18}$,
  $C_3$–$C_8$ cycloalkyl, or
  a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

$R^5$ is selected from:
  hydrogen, halogen, $C_1$–$C_4$ haloalkyl, hydroxy, $C_1$–$C_4$ alkoxy, $-NR^{14}R^{15}$, or $C_1$–$C_6$ alkyl substituted with 0–3 $R^{20}$;

$R^6$ and $R^7$ are independently selected from:
  H, $C_1$–$C_4$ alkyl, or $C_6$–$C_{10}$ aryl;

Alternately, $R^6$ and $R^7$ may be taken together to be
  1,2-phenylene substituted with 0–2 $R^5$,
  2,3-pyridinylene substituted with 0–2 $R^5$,
  3,4-pyridinylene substituted with 0–2 $R^5$, or
  5,6-pyrimidinylene substituted with 0–2 $R^5$;

$R^8$ is a substituent on nitrogen and is selected from
hydrogen,
$C_1$–$C_6$ alkyl substituted with 0–3 $R^{20}$,
$C_1$–$C_6$-alkylcarbonyl,
alkoxycarbonyl,
arylalkoxycarbonyl,
alkylaminocarbonyl,
arylsulfonyl,
heteroarylalkoxycarbonyl,
cycloalkoxycarbonyl,
heteroarylsulfonyl,
alkylsulfonyl, or
cycloalkylsulfonyl;

$R^{10}$ is selected from:
hydrogen,
$C_1$–$C_4$ alkoxy,
$C_1$–$C_6$ alkyl substituted with 0–4 $R^4$;

$R^{10a}$ is selected from hydrogen or $C_1$–$C_4$ alkyl;

$R^{10}$ and $R^{10a}$ can alternatively join to form —$(CH_2)_4$—, —$(CH_2)_5$—, —$CH_2CH_2N(R^{18})CH_2CH_2$—, or —$CH_2CH_2OCH_2CH_2$—;

$R^{11}$ is H, or $C_1$–$C_4$ alkyl;

$R^{12}$ is $C_1$–$C_4$ alkyl or $C_6$–$C_{10}$ aryl;

$R^{14}$ and $R^{15}$ are independently selected from H or $C_1$–$C_4$ alkyl;

$R^{17}$ is selected from:
hydrogen,
$C_1$–$C_6$ alkyl substituted with 0–3 $R^{17a}$
$C_1$–$C_6$ alkylcarbonyl substituted with 0–3 $R^{17a}$,
$C_1$–$C_6$ alkoxycarbonyl substituted with 0–3 $R^{17a}$,
phenoxycarbonyl substituted with 0–3 $R^{18}$;

$R^{17a}$ is selected from:
H,
$C_1$–$C_4$ alkyl,
aryl substituted with 0–5 $R^{18}$,
$C_3$–$C_8$ cycloalkyl
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

$R^{17b}$ is selected from:
aryl substituted with 0–5 $R^{18}$,
$C_3$–$C_8$ cycloalkyl
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;

$R^{18}$, when a substituent on carbon, is selected from one or more of the following:
phenoxy, benzyloxy, halogen, hydroxy, nitro, cyano, $C_1$–$C_4$ alkyl, $C_1$–$C_4$ alkoxy, —$CO_2H$, sulfonamide, $C_1$–$C_4$ alkyl substituted with —$NR^{10}R^{10a}$, —$NR^{10}R^{10a}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{11}$, —$NHSO_2R^{11}$,
phenyl, optionally substituted with halogen, $C_1$–$C_4$ alkyl, $C_1$–$C_4$ alkoxy, hydroxy or $NR^{10}R^{10a}$,
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$;
or $R^{18}$ may be a 3- or 4- carbon chain attached to adjacent carbons on the ring to form a fused 5- or 6-membered ring, said 5- or 6- membered ring being optionally substituted with halogen, $C_1$–$C_4$ alkyl, $C_1$–$C_4$ alkoxy, hydroxy, —$NR^{10}R^{10a}$, =O or =S when attached to a saturated carbon atom, or =O when attached to sulfur;

$R^{18}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{10}R^{10a}$, —$NR^{10}R^{10a}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl;

$R^{20}$ is selected from:
aryl substituted with 0–5 $R^{18}$,
a heterocycle selected from the group consisting of thienyl, pyridinyl, morpholinyl, furyl, thiazolyl, isothiazolyl, thiazolinyl, thiazolidinyl, isothiazolinyl, piperidinyl, pyrimidinyl, pyridazinyl, pyrazinyl, pyrrolidinyl, pyrrolyl, N-methylpyrrolyl, triazolyl, triazolidinyl, oxazolyl, isoxazolyl, oxazolinyl, isoxazolinyl, oxazolidinyl, oxadiazolyl, oxadiazolidinyl, imidazolyl, imidazolidinyl, said heterocyclic ring system being substituted with 0–5 $R^{18}$.

2. A compound of claim 1 wherein:
$R^1$ is selected from:
H, or
$C_1$–$C_4$ alkyl substituted with 0–3 $R^4$;
$R^2$ is selected from:
$C_2$–$C_4$ alkyl substituted with 0–3 $R^{17b}$,
—O—($C_1$–$C_6$ alkyl)—$R^{20}$,
—S—($C_1$–$C_6$ alkyl)—$R^{20}$,
—$CH_2O$—($C_1$–$C_5$ alkyl)—$R^{20}$, or
—$CH_2S$—($C_1$–$C_5$ alkyl)—$R^{20}$;
$R^3$ is selected from:
H,
$C_1$–$C_6$ alkyl substituted with 0–3 $R^{17b}$.

3. A compound of claim 1 selected from the group consisting of:
(a) N-[1(S)-(5-azabenzimidazol-2-yl)-2-(2-naphthyl)ethyl]-[3-hydroxyaminocarbonyl)-2(R)-isobutyl-3(S)-methyl]propanamide
(b) N-[1(S)-(2-imidazolyl)-2-(2-naphthyl)ethyl]-[3-hydroxyaminocarbonyl)-2(R)-isobutyl-3(S)-methyl]propanamide
(c) N-[1(S)-(5-methoxy-2-benzimidazolyl)-3-methylbutyl]-[3-(N-hydroxyaminocarbonyl)-2(R)-isobutyl-(3S)-methyl]propanamide, (d) N-[1(S)-(5-methoxy-2-benzimidazolyl)-2-phenylethyl]-[3-(N-hydroxyaminocarbonyl)-3(S)-hydroxy-2(R)-isobutyl]propanamide, (e) N-[1(S)-(5-methoxy-2-benzimidazolyl)-2,2,2-trimethylethyl]-[3-(N-hydroxyaminocarbonyl)-3(S)-hydroxy-2(R)-isobutyl]propanamide, (f) N-[1(S)-(5-chloro-2-benzimidazolyl)-2,2,2-trimethylethyl]-[3-(N-hydroxyaminocarbonyl)-3(S)-hydroxy-2(R)-isobutyl]propanamide, (g) N-[1(S)-(5-azabenzimidazol-2-yl)-2-(2-naphthyl)ethyl]-[3-(N-hydroxyaminocarbonyl)-3(S)-hydroxy-2(R)-isobutyl]propanamide, (h) N-[1(S)-(5-azabenzimidazol-2-yl)-2-(2-naphthyl)ethyl]-[3-(N-hydroxyaminocarbonyl)-3(S)-(2-picolyloxy)-2(R)-isobutyl]propanamide, (i) N-[1(S)-(5-azabenzimidazol-2-yl)-2-(2-naphthyl)ethyl]-[3-(N-hydroxyaminocarbonyl)-3(S)-(3-picolyloxy)-2(R)-isobutyl]propanamide, (j) N-[1(S)-(5-azabenzimidazol-2-yl)-2-(2-naphthyl)ethyl]-[3-(N-hydroxyaminocarbonyl)-3(S)-(4-picolyloxy)-2(R)-isobutyl]propanamide, (k) N-[1(S)-(5-azabenzimidazol-2-yl)-2-(2-naphthyl)ethyl]-[3-(N-hydroxyaminocarbonyl)-3(S)-benzyloxy-2(R)-isobutyl]propanamide, (l) N-[1(S)-(5-azabenzimidazol-2-yl)-2-(2-naphthyl)ethyl]-[3-(N-hydroxyaminocarbonyl)-3(S)-methyl-2(R)-isobutyl]propanamide, (m) [3-(N-hydroxyaminocarbonyl)-3(S)-phenpropyl-2(R)-isobutyl]propanamide, (n) N-[1(S)-(5-azabenzimidazol-2-yl)-2-(2-naphthyl)ethyl]-[3-(N-hydroxyaminocarbonyl)-3(S)-(2-pyridylpropyl)-2(R)-isobutyl]propanamide, (o) N-[1(S)-(5-azabenzimidazol-2-yl)-2-(2-naphthyl)ethyl]-[3-(N-hydroxyaminocarbonyl)-3(S)-propargyl-2(R)-isobutyl]propanamide, (p) N-[1(S)-(5-azabenzimidazolyl)-2-(2-naphthyl)ethyl]-[3-(N-hydroxyaminocarbonyl)-3(S)-allyl-2(R)-isobutyl]propanamide, (q) N-[1(S)-(5-azabenzimidazolyl)-2-(2-naphthyl)ethyl]-[3-(N-hydroxyaminocarbonyl)-3(S)-(1-pyrazolylpropyl)-2(R)-isobutyl]propanamide, and (r) N-[1(S)-(5-azabenzimidazolyl)-2-(2-naphthyl)ethyl]-[3-(N-hydroxyaminocarbonyl)-3(S)-(1-imidazolylpropyl)-2(R)-isobutyl]propanamide.

4. A pharmaceutical composition comprising a suitable pharmaceutical carrier and a therapeutically effective amount of a compound of claim 1.

5. A pharmaceutical composition comprising a suitable pharmaceutical carrier and a therapeutically effective amount of a compound of claim 2.

6. A pharmaceutical composition comprising a suitable pharmaceutical carrier and a therapeutically effective amount of a compound of claim 3.

7. A method of treating diseases mediated by matrix metalloproteinase and/or tumor necrosis factor in a mammal comprising administering to the mammal an effective amount of a compound of any one of claims 1 through 3.

8. A method of claim 7 wherein the disease is one mediated by matrix metalloproteinase.

9. A method of claim 7 wherein the disease is selected from rheumatoid arthritis, osteoarthritis, periodonitis, gingivitis, corneal ulceration or tumor invasion by secondary metastases.

10. A method of claim 7 wherein the disease is one mediated by tumor necrosis factor.

11. A method of claim 7 wherein the disease is selected from inflammation, fever, cardiovascular effects, hemorrhage, coagulation and acute phase response, cachexia and anorexia, an acute infection, a shock state, a graft versus host reaction or autoimmune disease.

* * * * *